US008227216B2

(12) United States Patent
Hu et al.

(10) Patent No.: US 8,227,216 B2
(45) Date of Patent: Jul. 24, 2012

(54) **METHODS OF USING *NANNOCHLOROPSIS* ALGAL STRAINS TO PRODUCE HYDROCARBONS AND FATTY ACIDS**

(75) Inventors: Qiang Hu, Chandler, AZ (US); Milton Sommerfeld, Chandler, AZ (US); Shan Qin, Gilbert, AZ (US)

(73) Assignee: Arizona Board of Regents For and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/274,281

(22) Filed: Oct. 14, 2011

(65) Prior Publication Data

US 2012/0070869 A1 Mar. 22, 2012

Related U.S. Application Data

(63) Continuation of application No. 13/194,691, filed on Jul. 29, 2011.

(60) Provisional application No. 61/369,533, filed on Jul. 30, 2010.

(51) Int. Cl.
*C12P 7/64* (2006.01)
*C12P 5/02* (2006.01)
(52) U.S. Cl. ........................................ 435/134; 435/167
(58) Field of Classification Search .................. None
See application file for complete search history.

(56) References Cited

U.S. PATENT DOCUMENTS

| 2007/0118916 | A1 | 5/2007 | Puzio et al. |
| 2009/0209015 | A1 | 8/2009 | Ramesha et al. |
| 2010/0028962 | A1 | 2/2010 | Hu et al. |
| 2010/0151539 | A1 | 6/2010 | Franklin et al. |

FOREIGN PATENT DOCUMENTS

WO WO-2008036654 A2 3/2008

OTHER PUBLICATIONS

Ackman, R. G., Jangaard, P. M., Hoyle, R. J. and Brockerhoff, H. 1964. Origin of marine fatty acids. I. Analyses of the fatty acids produced by the diatom *Skeletonema costatum*. J. Fish. Res. Bd. Can. 21: 747-756.
Bigogno et al. "Lipid and fatty acid composition of the green oleaginous alga *Parietochloris incisa*, the richest plant source of arachidonic acid," Phytochemistry. Jul. 2002;60(5):497-503.
Chiu et al., "Lipid accumulaton and CO2 utilization of *Nannochloropsis oculata* in response to CO2 aeration," Bioresour Technol. Jan. 2009;100(2):833-8.
Dunstan, G.A., J.K. Volkman, S.M. Barrett, and C.D. Garland. 1993. Changes in the lipid composition and maximization of the polyunsaturated fatty acid content of three microalgae grown in mass culture. J. Appl. Phycol. 5: 71-83.
Emdadi, D. and B. Berland. 1989. Variation in lipid class composition during batch growth of *Nannochloropsis salina* and *Pavlova lutheri*. Mar. Chem. 26: 215-225.

Fang et al., "Effects of organic carbon sources on cell growth and eicosapentaenoic acid content of *Nannochloropsis* sp.," Journal of Applied Phycology, (2004) 16:499-503.
Fang et al., "Growth and fatty acid composition of *Nannochloropsis* sp. Grown mixotrophically in fed-batch culture," Biotechnology Letters, 26: 2004,1319-1322.
Gouveia L, Oliveira AC Microalgae as raw material for biofuels production. J. 20 Ind. Microbiol. Biotechnol. 36: 269-274 2009.
Hodgson, P.A., Henderson, R.J., Sargent, J.R. & Leftley, J.W. (1991). Patterns of variation in the lipid class and fatty acid composition of *Nannochloropsis oculata* (Eustigmatophyceae) during batch culture. I. The growth cycle. J. Appl. Phycol., 3: 169-181.
Hsueh et al., Journal of photochemistry and photobiology. B, Biology 2009;95(1):33-9.
Hu et al., "Optiimization of growth and fatty acid composition of a unicellular marine picoplankton, *Nannochloropsis* sp., with enriched carbon sources," Biotech. Lett 25:421-425, 2003.
Hu, et al., "Response of growth and fatty acid compositions of *Nannochloropsis* sp. to environmental factors under elevated CO2 concentration," Biotechnol Lett (2006) 28:987-992.
International Search Report issued for PCT/US2011/45999, dated Dec. 19, 2011 (3 pages).
Kenyon, C. N. 1972. Fatty acid composition of unicellular strains of blue-green algae. J. Bacterid. 109: 827-834.
Lee, R. F. and Loeblich III, A. R. 1971. Distribution of 21 :6 hydrocarbon and its relationship to 22:6 fatty acid in algae. Phytochemistry. 10: 593-602.
Mata et al., "Microalgae for biodiesel production and other applicants: A Review," Renwable Sustainable Energy Rev., vol. 14: 210-232 (2009).
Orcutt, D. M. and Patterson, G. W. 1975. Sterol, fatty acid and elemental composition of diatoms grown in chemically media. Comp. Biochem. Physiol. 5OB: 579-583.
Parker, P. L., van Baalen, C. and Maurer, L. 1967. Fatty acids in eleven species of bluegreen algae: geochemical significance. Science. 155: 707-708.
Patil et al., Aquacult Int (2007) Fatty acid composition of 12 microalgae for possible use in aquaculture feed 15:1-9.
Pirt et al. "A tubular bioreactor for photosynthetic productino of biomass from carbon dioxide: design and performance," J. Chem. Tech. Biotechnol. (1983), 33B 35-58.
Pyle, et al., "Producing docosahexaenoic acid (DHA)-rich algae from biodiesel-derived crude glycerol: effects of impurities on DHA production and algal biomass composition," J. Agric. Food Chem., vol. 59(11): 3933-3939 (Jun. 11, 2008).
Radakovits et al., "Genetic Engeering of Algae for Enhanced Biofuel Production," Eukaryotic Cell, vol. 9(4): 486-501 (Apr. 2010).
Rodolfi et al., "Microalgae for Oil: Strain Selection, Induction of Lipid Synthesis and Outdoor Mass Cultivation in a Low-Cost Photobioreactor," Biotechnol Bioeng. Jan. 1, 2009;102(1):100-12 2009.

(Continued)

*Primary Examiner* — Tekchand Saidha
*Assistant Examiner* — MD. Younus Meah
(74) *Attorney, Agent, or Firm* — Tom Gallegos, Esq.; Justin Kniep, Esq.; Colleen Superko, Esq.

(57) ABSTRACT

The present invention provides methods and compositions for production of algal-based medium chain fatty acids and hydrocarbons. More specifically, the invention relates to a *Nannochloropsis* algal strain and mutants that produces high amounts of C16 fatty acids and hydrocarbons. The present invention provides methods and compositions for production of algal-based medium chain fatty acids and hydrocarbons. More specifically, the invention relates to a *Nannochloropsis* algal strain and mutants that produces high amounts of C16 fatty acids and hydrocarbons.

12 Claims, 19 Drawing Sheets

OTHER PUBLICATIONS

Roncarati et al, "Fatty Acid Composition of Different Microalgae Strains (*Nannoochloropsis*, sp., *Nannocloropsis oculata* (Droop_ Hibbertd, *Nannochloris atomus* Butcher and *Isochrysis* sp.) According to the Culture Phase and the Carbon Dioxiod Concentration," 2004 (12 pages).

Suen, Y., J. S. Hubbard, G. Holzer, and T. G. Tornabene. 1987. Total lipid production of the green alga *Nannochloropsis* sp. QII under different nitrogen regimes. J. Phycol. 23:289-296.

Tornabene, T. G., Kates, M. and Volcanl, B. E. 1974. Sterol aliphatic hydrocarbons, and fatty acids of a nonphotosynthetic diatom, *Nitzschia alba*. Lipids. 9: 279-284.

Volkman et al. 1981, "Sterol and fatty acid composition of four marine haptophycean algae". J. Mar. Biol. Ass. U. K. 61 : 509-527.

Xu et al., "Growth characteristics and eicosapentaenoic acid production by *Nannochloropsis* sp. in mixotrophic condition," Biotechnology Letters, 2004, 26: 51-53 2004.

Yu, et al., "Identification of the alga known as *Nannochloropsis* Z-1 isolated from a prawn farm in Hainan, China as *Chlorella*," Wordl J. Microbiol. Biotechnol., vol. 23: 207-210 (2007).

7A

7B

Fig. 17 ITS sequence of *Nannochloropsis* sp. LRB-AZ 0202.0 (SEQ ID NO:1), comprising 18S ribosomal RNA gene, partial sequence; internal transcribed spacer 1, 5.8S ribosomal RNA gene, and internal transcribed spacer 2, complete sequence; and 28S ribosomal RNA gene, partial sequence CCGTCGCACCTACCGATTGAATGATTCGGTGAAGCTTTCGGATTGCGCCAC
TGGCCTCGGTCGGCAGCGTGAGAAGTTATCTAAACCTCATCATTTAGAGG
AAGGTGAAGTCGTAACAAGGTTTCCGTAGGTGAACCTGCGGAAGGATCAT
TACCAAAACACATCATGCCTCCTGGCGTATGCTTCGAGGCATTACACTTCA
CAACCTGTGCATTGTTTACTCCTGTGAACGCTATACACGCACGTGCTCCCG
GCCACGCCCTGCGATGGTTGCTTTGGATGGTTCCTCGGAACACGTCGAAG
CCGTGGCCGAATGTGGGAGGGCGTCTCTAAATAACCTCAAACACCATTCG
CAACATTTTATCAACCTTTCCAAACCGATTGTTTATACTTCATTCAAGGCTT
TTCTAGTCTTCGGACGGAAAAAGCCTGGTGCATGTTTCCATGCGAAACGA
GCGCCCGCAATGAAAATACAACTTTCAGCAACGGATGTCTTGGCTCCCAC
AACGATGAAGAACGCAGCGAAATGCGATACGTAATGCGAATTGCAGAAT
TCCGCGAGTCATCAAACCTTTGAACGCACCTTGCGCTTTCGGGATATGCCC
GTTAGCATGTTTGTTGGAGTGTCTGTTAACCCCAATCACCACCTTGTTGTG
ACTTCAGAGTCATGCCAAGCGGTCGGTGGACGTTACTTGCTCCCGATACTT
CGCCCGCTGCGAATTCTGTTGTCACCTCCTCTGACGAGGAAGTGGCCAGA
AGCTGGAGTGCGGGCGTGGAGTGAAGTAGGGCCGGCCACATACAGTCACT
GGGACCACGCAACTCCTAGAGCTGCCCCCGTGAACGTGACGAGTCTTCTA
ATCAAGGCAATCCGTTTGAGGTCTAAAAGGTGCTCGTTTGACGGAAGCGC
TAGTCTACACCAAACAGTTTCGACTTGGCGGCATCTTCTCGGTGACGTAAC
AAACACCGAGAAAGCCTTTGGACTGATCCTGGCACTTGTTGCCGTGTCATT
CCATCTCCAATTCGGACCTCCAATCAAGCAAGGCTACCCGCTGAATTTAA
GCATATAACTAAGCGGAGGAAAAGAAACTAACCAGGATTCCCCTAGTAAC
GGCGAGTGAAGCGG Fig 18 ITS sequence of *Nannochloropsis* sp. LRB-AZ 0202.2 (SEQ ID NO:2), comprising 18S ribosomal RNA gene, partial sequence; internal transcribed spacer 1, 5.8S ribosomal RNA gene, and internal transcribed spacer 2, complete sequence; and 28S ribosomal RNA gene, partial sequence.

```
CCGTCGCACCTACCGATTGAATGATTCGGTGAAGCTTTCGGATTGCGCCAC
TGGCCTCGGTCGGCAGCGTGAGAAGTTATCTAAACCTCATCATTTAGAGG
AAGGTGAAGTCGTAACAAGGTTTCCGTAGGTGAACCTGCGGAAGGATCAT
TACCAAAACACATCATGCCTCCTGGCGTATGCTTCGAGGCATTACACTTCA
CAACCTGTGCATTGTTTACTCCTGTGAACGCTATACACGCACGTGCTCCCG
GCCACGCCCTGCGATGGTTGCTTTGGATGGTTCCTCGGAACACGTCGAAG
CCGTGGCCGAATGTGGGAGGGCGTCTCTAAATAACCTCAAACACCATTCG
CAACATTTTATCAACCTTTCCAAACCGATTGTTTATACTTCATTCAAGGCTT
TTCTAGTCTTCGGACGGAAAAAGCCTGGTGCATGTTTCCATGCGAAACGA
GCGCCCGCAATGAAAATACAACTTTCAGCAACGGATGTCTTGGCTCCCAC
AACGATGAAGAACGCAGCGAAATGCGATACGTAATGCGAATTGCAGAAT
TCCGCGAGTCATCAAACCTTTGAACGCACCTTGCGCTTTCGGGATATGCCC
GTTAGCATGTTTGTTGGAGTGTCTGTTAACCCCAATCACCACCTTGTTGTG
ACTTCAGAGTCATGGCAAGCAGTCGGTGGACGTTACTTGCTCCCGATACTT
CGCCCGCTGCGAATTCTGTTGTCACCTCCTCTGACGAGGAACTGGCCAGA
AGCTGGAGTGCGGGCGTGGAGTGAAGTAGGGCCGGCCACATACAGTCACT
GGGACCACGCAACTCCTAGAGCTGCCCCGTGAACGTGACGAGTCTTCTA
ATCAAGGCAATCCGTTTGCGGTCTAAAAGGTGCTCGTTTGATGGAAGCGC
TAGTCTACACCAAACAGTTTCGACTTGGCGGCATCTTCTCGGTGACATAAC
AAACACCGAGAAAGCCTTTGGACTGATCCTGGCACTCGTTGCCGTGTCATT
CCATCTCCAATTCGGACCTCCAATCAAGCAAGGCTACCCGCTGAATTTAA
GCATATAACTAAGCGGAGGAAAAGAAACTAACCAGGATTCCCCTAGTAAC
GGCGAGTGAAGCGG
```

Fig 19 ITS sequence of *Nannochloropsis* sp. LRB-AZ 0202.3 (SEQ ID NO:3), comprising 18S ribosomal RNA gene, partial sequence; internal transcribed spacer 1, 5.8S ribosomal RNA gene, and internal transcribed spacer 2, complete sequence; and 28S ribosomal RNA gene, partial sequence.

```
CCGTCGCACCTACCGATTGAATGATTCGGTGAAGCTTTCGGATTGCGCCAC
TGGCCTCGGTCGGCAGCGTGAGAAGTTATCTAAACCTCATCATTTAGA
GGAAGGTGAAGTCGTAACAAGGTTTCCGTAGGTGAACCTGCGGAAGGATC
ATTACCAAAACACATCATGCCTCCTGGCGTACGCTTCGAGGCATTACACTT
CACAACCTGTGCATTGTTTACTCCTGTGAACGCTATACACGCACGTGCTCC
CGGCCACGCCCTGCGATGGTTGCTTTGGATGGTTCCTCGGAACACGTCGA
AGCCGTGGCCGAATGTGGGAGGGCGTCTCTAAATAACCTCAAACACCATT
CGCAACATTTATCAACCTTTCCAAACCGATTGTTTATACTTCATTCAAGG
CTTTTCTAGTCTTCGGACGGAAAAGCCTGGAGCATGTTTCCATGCG
AAACGAGCGCCCGCAATGAAAATACAACTTTCAGCAACGGATGTCTTGGC
TCCCACAACGATGAAGAACGCAGCGAAATGCGATACGTAATGCGAATTGC
AGAATTCCGCGAGTCATCAAACCTTTGAACGCACCTTGCGCTTTCGGGATA
TGCCCGTTAGCATGTTTGTTGGAGTGTCTGTTAACCCCAATCACCACCTTG
TTGTGACTTCAGAGTCATGCCAAGCGGTCGGTGGACGTTACTTGCTCCCGA
TACTTCGCCCGCTGCGAATTCTGTTGTCACCTCCTCTGACGAGGAAGTGGC
CAGAAGCTGGAGTGCGGGCGTGGAGTGAAGTAGGGCCGGCCACATA
CAGTCACTGGGACCACGCAACTCCTAGAGCTGCCCCGTGAACGTGACGA
GTCTTCTAATCAAGGCAATCCGTTTGAGGTCTAAAAGGTGCTCGTTTGACG
GAAGCGCTAGTCTACACCAAACAGTTTCGACTTGGCGGCATCTTCTCGGTG
ACGTAACAAACACCGAGAAAGCCTTTGGACTGATCCTGGCACTTGTTGCC
GTGTCATTCCATCTCCAATTCGGACCTCCAATCAAGCAAGGCTACCCGCTG
AATTTAAGCATATAACTAAGCGGAGGAAAAGAAACTAACCAGGATTCCCC
TAGTAACGGCGAGTGAAGCGG
```

Fig 20. Phylogenetic tree of *Nannochloropsis* spp. LRB-AZ 0202.0, LRB-AZ 0202.2, LRB-AZ 0202.3 based on ITS sequences.
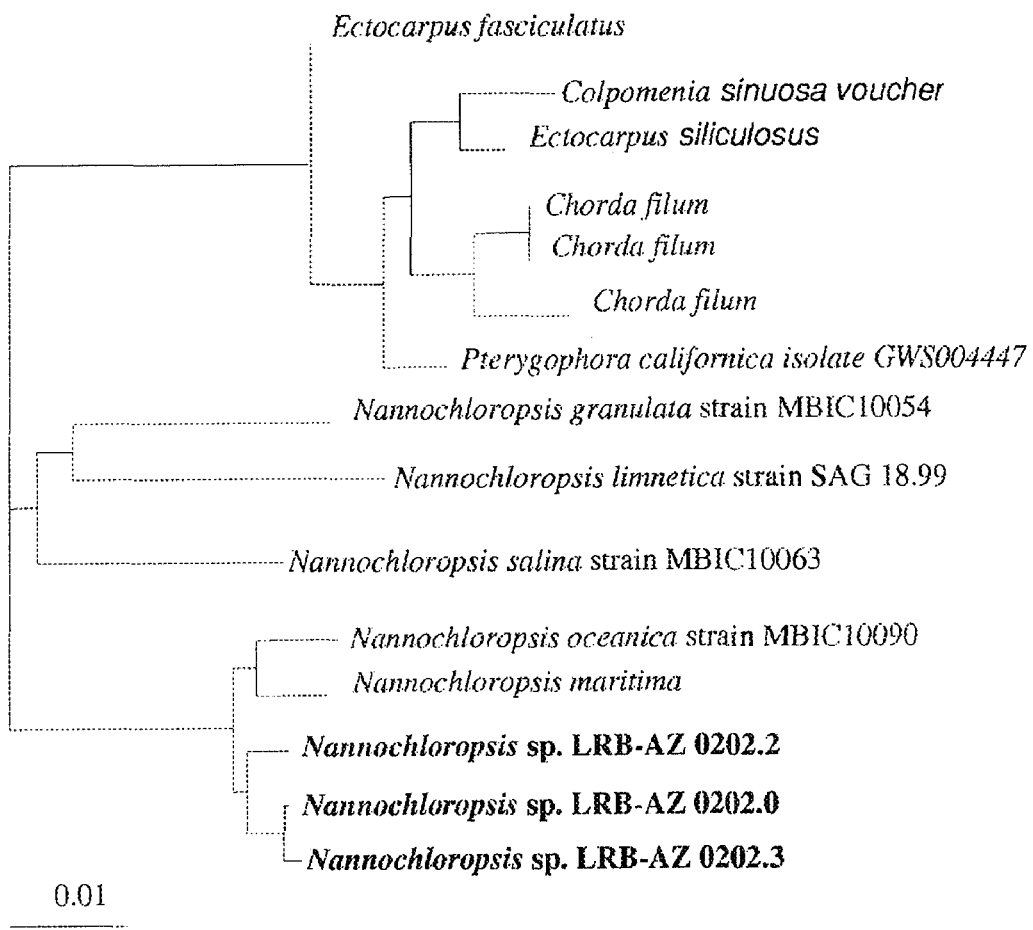

SEQUENCE LISTING

<160> NUMBER OF SEQ ID NOS: 5

<210> SEQ ID NO 1
<211> LENGTH: 1123
<212> TYPE: DNA
<213> ORGANISM: Nannochloropsis sp.

<400> SEQUENCE: 1

```
ccgtcgcacc taccgattga atgattcggt gaagctttcg gattgcgcca ctggcctcgg      60
tcggcagcgt gagaagttat ctaaacctca tcatttagag gaaggtgaag tcgtaacaag     120
gtttccgtag gtgaacctgc ggaaggatca ttaccaaaac acatcatgcc tcctggcgta     180
tgcttcgagg cattacactt cacaacctgt gcattgttta ctcctgtgaa cgctatacac     240
gcacgtgctc ccggccacgc cctgcgatgg ttgctttgga tggttcctcg gaacacgtcg     300
aagccgtggc cgaatgtggg agggcgtctc taaataacct caaacaccat tcgcaacatt     360
ttatcaacct ttccaaaccg attgtttata cttcattcaa ggcttttcta gtcttcggac     420
ggaaaaagcc tggtgcatgt ttccatgcga acgagcgcc cgcaatgaaa atacaacttt     480
cagcaacgga tgtcttggct cccacaacga tgaagaacgc agcgaaatgc gatacgtaat     540
gcgaattgca gaattccgcg agtcatcaaa cctttgaacg caccttgcgc tttcgggata     600
tgcccgttag catgtttgtt ggagtgtctg ttaaccccaa tcaccacctt gttgtgactt     660
cagagtcatg ccaagcggtc ggtggacgtt acttgctccc gatacttcgc ccgctgcgaa     720
ttctgttgtc acctcctctg acgaggaagt ggccagaagc tggagtgcgg gcgtggagtg     780
aagtagggcc ggccacatac agtcactggg accacgcaac tcctagagct gccccgtga     840 acgtgacgag tcttctaatc aaggcaatcc gtttgaggtc taaaaggtgc tcgtttgacg     900
gaagcgctag tctacaccaa acagtttcga cttggcggca tcttctcggt gacgtaacaa     960
acaccgagaa agcctttgga ctgatcctgg cacttgttgc cgtgtcattc catctccaat    1020
tcggacctcc aatcaagcaa ggctacccgc tgaatttaag catataacta agcggaggaa    1080
aagaaactaa ccaggattcc cctagtaacg gcgagtgaag cgg                      1123
```

<210> SEQ ID NO 2
<211> LENGTH: 1123
<212> TYPE: DNA
<213> ORGANISM: Nannochloropsis sp.

<400> SEQUENCE: 2

```
ccgtcgcacc taccgattga atgattcggt gaagctttcg gattgcgcca ctggcctcgg      60
tcggcagcgt gagaagttat ctaaacctca tcatttagag gaaggtgaag tcgtaacaag     120
gtttccgtag gtgaacctgc ggaaggatca ttaccaaaac acatcatgcc tcctggcgta     180
tgcttcgagg cattacactt cacaacctgt gcattgttta ctcctgtgaa cgctatacac     240
gcacgtgctc ccggccacgc cctgcgatgg ttgctttgga tggttcctcg gaacacgtcg     300
aagccgtggc cgaatgtggg agggcgtctc taaataacct caaacaccat tcgcaacatt     360
ttatcaacct ttccaaaccg attgtttata cttcattcaa ggcttttcta gtcttcggac     420
ggaaaaagcc tggtgcatgt ttccatgcga acgagcgcc cgcaatgaaa atacaacttt     480
cagcaacgga tgtcttggct cccacaacga tgaagaacgc agcgaaatgc gatacgtaat     540
gcgaattgca gaattccgcg agtcatcaaa cctttgaacg caccttgcgc tttcgggata     600
tgcccgttag catgtttgtt ggagtgtctg ttaaccccaa tcaccacctt gttgtgactt     660
```

| cagagtcatg gcaagcagtc ggtggacgtt acttgctccc gatacttcgc ccgctgcgaa | 720 |
| ttctgttgtc acctcctctg acgaggaact ggccagaagc tggagtgcgg gcgtggagtg | 780 |
| aagtagggcc ggccacatac agtcactggg accacgcaac tcctagagct gcccccgtga | 840 |
| acgtgacgag tcttctaatc aaggcaatcc gtttgcggtc taaaaggtgc tcgtttgatg | 900 |
| gaagcgctag tctacaccaa acagtttcga cttggcggca tcttctcggt gacataacaa | 960 |
| acaccgagaa agcctttgga ctgatcctgg cactcgttgc cgtgtcattc catctccaat | 1020 |
| tcggacctcc aatcaagcaa ggctacccgc tgaatttaag catataacta agcggaggaa | 1080 |
| aagaaactaa ccaggattcc cctagtaacg gcgagtgaag cgg | 1123 |

<210> SEQ ID NO 3
<211> LENGTH: 1123
<212> TYPE: DNA
<213> ORGANISM: Nannochloropsis sp.

<400> SEQUENCE: 3

| ccgtcgcacc taccgattga atgattcggt gaagctttcg gattgcgcca ctggcctcgg | 60 |
| tcggcagcgt gagaagttat ctaaacctca tcatttagag gaaggtgaag tcgtaacaag | 120 |
| gtttccgtag gtgaacctgc ggaaggatca ttaccaaaac acatcatgcc tcctggcgta | 180 |
| cgcttcgagg cattcacttt cacaacctgt gcattgttta ctcctgtgaa cgctatacac | 240 |
| gcacgtgctc ccggccacgc cctgcgatgg ttgctttgga tggttcctcg gaacacgtcg | 300 |
| aagccgtggc cgaatgtggg agggcgtctc taaataaccct caaacaccat cgcaacatt | 360 |
| ttatcaacct ttccaaaccg attgtttata cttcattcaa ggcttttcta gtcttcggac | 420 |
| ggaaaaagcc tggagcatgt ttccatgcga acgagcgcc cgcaatgaaa atacaacttt | 480 |
| cagcaacgga tgtcttggct cccacaacga tgaagaacgc agcgaaatgc gatacgtaat | 540 |
| gcgaattgca gaattccgcg agtcatcaaa cctttgaacg caccttgcgc tttcgggata | 600 |
| tgcccgttag catgtttgtt ggagtgtctg ttaaccccaa tcaccacctt gttgtgactt | 660 |
| cagagtcatg ccaagcggtc ggtggacgtt acttgctccc gatacttcgc ccgctgcgaa | 720 |
| ttctgttgtc acctcctctg acgaggaagt ggccagaagc tggagtgcgg gcgtggagtg | 780 |
| aagtagggcc ggccacatac agtcactggg accacgcaac tcctagagct gcccccgtga | 840 |
| acgtgacgag tcttctaatc aaggcaatcc gtttgaggtc taaaaggtgc tcgtttgacg | 900 |
| gaagcgctag tctacaccaa acagtttcga cttggcggca tcttctcggt gacgtaacaa | 960 |
| acaccgagaa agcctttgga ctgatcctgg cacttgttgc cgtgtcattc catctccaat | 1020 |
| tcggacctcc aatcaagcaa ggctacccgc tgaatttaag catataacta agcggaggaa | 1080 |
| aagaaactaa ccaggattcc cctagtaacg gcgagtgaag cgg | 1123 |

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

| ccgtcgcacc taccgattga at | 22 |

<210> SEQ ID NO 5
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 5
ccgcttcact cgccgttact a                                              21
```

METHODS OF USING *NANNOCHLOROPSIS* ALGAL STRAINS TO PRODUCE HYDROCARBONS AND FATTY ACIDS

CROSS REFERENCE TO RELATED APPLICATIONS

This application is a continuation of and claims the benefit of U.S. patent application Ser. No. 13/194,691, filed on Jul. 29, 2011, which is itself a non-provisional application of and claims the benefit of U.S. Provisional Application No. 61/369,533, filed Jul. 30, 2010, the entire contents of which are all hereby incorporated by reference herein.

SEQUENCE LISTING

The instant application contains a Sequence Listing which has been submitted in ASCII format via EFS-Web and is hereby incorporated by reference in its entirety. Said ASCII copy, created on Nov. 7, 2011, is named 22048US3.txt and is 5,474 bytes in size.

BACKGROUND

JP-8 is a kerosene-type military jet fuel derived from petroleum and is being used as the primary fuel for land-based air and ground forces (e.g., aircraft, ground vehicles, and equipment). The US Department of Defense (DOD) is the single largest oil consuming government body in the US, consuming over 90 million barrels of JP-8 in fiscal 2006, which represents about 15% of kerosene-based jet fuel produced by the U.S.

Commercial jet fuel similar to JP-8 in chemical composition is largely consumed by the U.S. commercial (corporate/private) aviation industry with passenger and cargo carriers burning nearly 500 million barrels of jet fuel in 2005. As having already consumed over 80% of its proven oil reserves, the U.S. now imports more than 60% of its oil. It is anticipated that within 20 years the U.S. will be importing from 80% to 90% of its oil. Much of this imported oil is supplied from nations in politically-volatile regions of the world where political instability, human rights abuses, and terrorism are the constant threat to a stable oil supply for the U.S.

Over $250 billion is spent on foreign oil annually, representing a third of the growing US trade deficit and an increasing burden on the US economy. Although the U.S. can continue to increasingly import foreign oil, global oil supplies are not infinite. Even based upon an optimistic estimate of the world oil resource of approximately 2,200-3,900 billion barrels, nearly twice the proven reserve, the world supply of petroleum oil will be depleted within 40 years. Demand for oil by emerging and rapidly growing economies such as in China, India, and South America, is also increasing competition and price volatility for limited global supplies. The severity of potential impacts of oil reduction on U.S. military operations, national security, and the growing economy will depend on how much, how quickly, and how far in advance of this event we are able to provide a wide range of renewable, affordable alternatives to JP-8 and other fossil fuels.

Oil-rich crops and algae are widely regarded as the most promising biological systems for cost-effective, sustainable production of biodiesel particularly for transportation. However, biodiesel produced from current available oil crop-based feedstocks and commercial processes is not suitable as a JP-8 surrogate fuel for military and commercial aviation applications due to its lower energy density and unacceptable cold-flow features. The disqualification of biodiesel as an alternative to JP-8 stems from the fact that the former contains mostly methyl esters of C16 and C18 fatty acids, whereas the latter has the main chemical components of C9 to C14 hydrocarbons. Compared to C9 to C14 hydrocarbons, oxygenated methyl esters of C16 and C18 fatty acids not only decrease energy density of the fuel, but also are responsible for high fuel viscosity, high flash point, and high freezing points (>−50° C.).

Biodiesel can be processed into JP-8 surrogate fuel through thermal, catalytic, and/or enzymatic processes. However, the subsequent secondary processing is neither cost-effective nor energy-efficient and consumes large quantities of fossil fuels with an energy conversion efficiency of 8% to 15%. This results in alternative jet fuel being prohibitively expensive and having unacceptably low energy efficiency. Clearly, transforming algae/plant-based oil or biodiesel into an affordable alternative to petroleum-derived JP-8 has great potential, but this will require significant innovations and improvements to current feedstock production systems and subsequent downstream processes to enhance oil conversion efficiency, while driving production costs down.

One way to increase energy conversion efficiency while reducing production costs of crop oil derived JP-8 surrogate fuel is to introduce certain feedstock oils that may naturally consist of large amounts of medium-chain fatty acids (C10 to C14). The medium-chain fatty acids may require little cracking treatment, which is otherwise required process to break long-chain molecules into shorter ones. Coconut and palm kernel oils have turned out to be the exceptions from common oil crops by containing high concentrations (55~69% of total fatty acids) of medium-chain (C12 and C14) fatty acids/esters. The world production of coconut oil was about 50 million metric tons in 1999, and the production of palm kernel oil was about 3.8 million tons in 2005. Indonesia, Malaysia, Philippines, and India are the major producers of coconut and palm kernel oils. These oils are mainly used for domestic consumption as food and cooking/frying oil. In the U.S. and other western countries, coconut and palm kernel oils are largely used in the manufacture of margarine and other fat/oil products, as well as in cosmetics, soaps, detergents and shampoos. Although coconut and palm kernel oils are being exploited for production of biodiesel and are considered to be kerosene-based jet fuel substitute, they are unlikely to be used as a major feedstock for jet fuel production due to limited supplies (Shay 1993; Srivastava & Prasad 2000).

An alternative is to make more medium-chain fatty acids through genetic manipulations of oil crops. However, the efforts made thus far with oil-crops have resulted in little commercial significance. This is due mainly to the lack of clear understanding of cellular/subcellular regulatory networks that may provide 'global' control over complex biochemical pathways, which may lead to partitioning of photosynthetically-fixed carbon specifically into the formation and accumulation of lipids/oil rather than biosynthesis of protein or carbohydrate. Lack of effective molecular genetic tools and methodologies is another major reason for unsuccessful strain improvement.

Microalgae may be a promising source of feedstock for biofuels because of a) their high lipid/oil contents (40 to 60% of dry weight); b) high specific growth rates (1 to 3 doubling time per day); c) the ability to thrive in saline/brackish water and utilize nutrients (N, P, and CO2) from waste-streams (e.g., wastewater and flue gases from fossil fuel-fired power plants) for growth, and use marginal lands (desert, arid- and semi-arid lands) for wide-scale production all year around; and d) co-production of value-added products (e.g., biopolymers, proteins, polysaccharide, pigments). However, algal oils studied for biofuels so far are rather similar in chemical and physical properties to that of common crop oils, which are enriched with C16 to 18 fatty acids/esters.

SUMMARY

The present invention relates to methods and compositions for the use of *Nannochloropsis* algal strains for the production of large amounts of medium chain length fatty acids. In particular, it has been discovered that in excess of 50% of the fatty acids produced by *Nannochloropsis* strain LARB-AZ 0202.0 and mutants thereof are C16 fatty acids. C16 fatty acids are valuable because they are easily converted to biofuels and other useful and important hydrocarbon based products. This heretofore unknown strain of *Nannochloropsis* and its mutants can thus be used in the production of fatty acids for use in biofuel production.

The present invention provides methods and compositions for production of algal-based medium chain fatty acids and hydrocarbons. More specifically, the invention relates to a *Nannochloropsis* algal strain and mutants that produces high amounts of C16 fatty acids and hydrocarbons. In particular embodiments, the present invention relates to a method for producing algal medium chain length fatty acids or hydrocarbons, comprising:
   (a) culturing a first algal culture consisting of *Nannochloropsis* strain LARB-AZ 0202.0 deposited at ATCC Deposit Number PTA-11048 or a mutant thereof deposited at ATCC Deposit Number PTA 11049 or ATCC Deposit Number PTA-11050, or a combination of two or more said *Nannochloropsis* strains (LARB-AZ 0202.2; LARB-AZ 0202.3) wherein said first algal strain produces at least a first medium chain length fatty acid subset wherein at least 60% of the fatty acids in said subset are of a chain length of C16, wherein the culturing is conducted under conditions suitable to promote production of the first medium chain fatty acid subset; and
   (b) extracting oil from the first algal strain to produce a medium chain length combination; wherein the medium chain length combination comprises carbon chain length C10, C12, C14 and C16 fatty acids or hydrocarbons, wherein said oil is enriched for C16 fatty acids such that greater than 60% of the fatty acids in said oil are C16 fatty acids; said method optionally further comprising converting oil extracted from the first algal strain into a hydrocarbon fraction and refining the hydrocarbon fraction to produce one or more fractions enriched in medium chain length hydrocarbons, wherein the one or more fractions comprises one or more fractions enriched in carbon chain length C10, C12, C14 and C16 hydrocarbons.

While in preferred embodiments, the methods employs only *Nannochloropsis* strain LARB-AZ 0202.0 either alone or in combination with mutants thereof, in further embodiments, the method may further comprise culturing one or more further algal strains that produce a second medium chain length fatty acid subset wherein at least 20% of the fatty acids in said subset are medium chain length fatty acids wherein the culturing is conducted under conditions suitable to promote production of the second medium chain fatty acid subset. An example of these conditions would be culturing under conditions cell comprising 1.5 g/L NaNO$_3$ and at a light intensity of about 350 µmol photons m$^{-2}$ s$^{-1}$, and initial N$_2$ gas concentration of the cell culture of about 0.01 g/L.

In the various methods, the first algal strain and the one or more further algal strains may be cultured as separate cultures or are cultured as a co-culture. Where the method employs multiple *Nannochloropsis* strains e.g., *Nannochloropsis* strain LARB-AZ 0202.0 and mutants thereof, the multiple strains may be co-cultured or may be cultured in separate cultures.

In the methods of the present invention, the one or more fractions further comprises one or more fractions enriched in carbon chain length C16 hydrocarbons.

The methods of the present invention may further comprise producing kerosene from the one or more fractions enriched in medium chain length hydrocarbons.

In exemplary embodiments, the methods may further comprise isolating an algal biomass residue and/or short-chain hydrocarbon molecules and/or glycerol produced in said method.

The methods of the invention using *Nannochloropsis* strain LARB-AZ 0202.0 or mutants thereof may be combined with methods that use one or more further algal strains comprises at least a second algal strain and a third algal strain that is different from said first algal strain and independently is selected from the group consisting of *Pinguiococcus pyrenoidosus, Aphanocapsa* sp., *Biddulphia aurita, Crypthecodinium* sp., *Emiliania huxleyi, Nitzschia alba, Prymnesium parvum, Skeletonema costatum*, and *Trichodesmium erythraeum*.

Also contemplated is a method for producing algal medium chain length fatty acids, comprising:
   (a) culturing *Nannochloropsis* strain LARB-AZ 0202.0 deposited under ATCC Deposit Number PTA-11048 or a mutant thereof or a combination of said *Nannochloropsis* strain LARB-AZ 0202.0 and one or more mutants thereof under conditions suitable to promote production of medium chain length fatty acids enriched in C16 fatty acids; and
   (b) extracting oil from the cultured *Nannochloropsis* strain LARB-AZ 0202.0 or the one or more mutants thereof wherein the extracted oil comprises C14 and C16 chain length fatty acids.

In specific embodiments, the mutant of *Nannochloropsis* strain LARB-AZ 0202.0 is a LARB-AZ 0202.2 deposited at ATCC Deposit Number PTA-11049 or a LARB-AZ 0202.3 deposited at ATCC Deposit Number PTA-11050. The method may further comprise converting oil extracted from *Nannochloropsis* strain LARB-AZ 0202.0 or a mutant thereof into a hydrocarbon fraction, and optionally refining the hydrocarbon fraction to produce one or more fractions enriched in medium chain length hydrocarbons, wherein the one or more fractions comprises at least one fraction enriched in carbon chain length C16 hydrocarbons. More particularly, the one or more fractions may comprise at least one fraction enriched in carbon chain length C16 hydrocarbons, said method optionally further comprising producing kerosene from the one or more fractions enriched in medium chain length hydrocarbons. Further the method may comprise isolating algal biomass.

Also described herein are methods of producing algal medium chain length fatty acids or hydrocarbons, comprising
   (a) culturing *Nannochloropsis* strain LARB-AZ 0202.0 deposited under ATCC Deposit Number PTA-11048 or a mutant thereof or a combination of said *Nannochloropsis* strain LARB-AZ 0202.0 and one or more mutants thereof under conditions suitable to promote production of medium chain length fatty acids enriched for C16 fatty acids;
   (b) culturing one or more further algal strains that can produce and accumulate large quantities of C14 chain length fatty acids, wherein the culturing is conducted under conditions suitable to promote production of the C14 chain length fatty acids; and (c) culturing one or more further algal strains that can produce and accumulate large quantities of C10 and/or C12 chain length fatty acids, wherein the culturing is conducted under conditions suitable to promote production of the C10 and/or C12 chain length fatty acids; and (d) extracting oil from the cultured *Nannochloropsis* strain LARB-AZ 0202.0 or a mutant thereof and the one or more further algal strains to produce a medium chain length combination; wherein the medium chain length combination comprises carbon chain length C14 and one or more of C10 and C12 fatty acids or hydrocarbons;

said method optionally further comprising converting the medium chain length combination into a hydrocarbon fraction and further comprising refining the hydrocarbon fraction to produce one or more fractions enriched in medium chain length hydrocarbons, wherein the one or more fractions comprises one or more fractions enriched in carbon chain length C16, C10, C12, and C14 hydrocarbons.

In particular embodiments the mutant of *Nannochloropsis* strain LARB-AZ 0202.0 is a LARB-AZ 0202.2 deposited at ATCC Deposit Number PTA-11049 or a LARB-AZ 0202.3 deposited at ATCC Deposit Number PTA-11050 or a combination of both.

In specific embodiments, the medium chain length combination is prepared by combining oil extracted from the *Nannochloropsis* strain LARB-AZ 0202.0 or a mutant thereof and the one or more further algal strains after oil extraction or by extracting oil from a culture comprising both the *Nannochloropsis* strain LARB-AZ 0202.0 or a mutant thereof and the one or more further algal strains. More particularly, the one or more fractions further comprises one or more fractions enriched in carbon chain length C16 hydrocarbons and optionally further comprising producing kerosene from the one or more fractions enriched in medium chain length hydrocarbons. By way of example, the one or more further algal strains comprises a second algal strain and a third algal strain, wherein the third algal strain is selected from the group consisting of *Aphanocapsa* sp., *Biddulphia aurita*, *Crypthecodinium* sp., *Emiliania huxleyi*, *Nitzschia alba*, *Prymnesium parvum*, *Skeletonema costatum*, and *Trichodesmium erythraeum*.

Also contemplated is a composition comprising *Nannochloropsis* strain LARB-AZ 0202.0 deposited at ATCC Deposit Number PTA-11048. Another embodiment contemplates a composition comprising a *Nannochloropsis* strain LARB-AZ 0202.2 deposited at ATCC Deposit Number PTA-11049 or *Nannochloropsis* strain LARB-AZ 0202.3 deposited at ATCC Deposit Number PTA-11050, or a combination of LARB-AZ 0202.2 and LARB-AZ 0202.3.

In yet another embodiment, there is a composition that comprises *Nannochloropsis* strain LARB-AZ 0202.0 deposited at ATCC Deposit Number PTA-11048 and further comprises a *Nannochloropsis* strain LARB-AZ 0202.2 deposited at ATCC Deposit Number PTA-11049 or *Nannochloropsis* strain LARB-AZ 0202.3 deposited at ATCC Deposit Number PTA-11050, or a combination of LARB-AZ 0202.2 and LARB-AZ 0202.3.

Any of the aforementioned compositions may further comprise two or more isolated algal strains selected from the group consisting of *Pinguiococcus pyrenoidosus*, *Aphanocapsa* sp., *Biddulphia aurita*, *Crypthecodinium* sp., *Emiliania huxleyi*, *Nitzschia alba*, *Prymnesium parvum*, *Skeletonema costatum*, and *Trichodesmium erythraeum*, wherein the *Nannochloropsis* strain LARB-AZ 0202.0 or a mutant thereof and the two or more algal strains make up at least 90% of the algae present in the composition. For example, the two or more isolated algal strains comprise one or both of *Crypthecodinium* sp. and *Trichodesmium erythraeum*. In other embodiments, the two or more isolated algal strains further comprise an algal strain selected from the group consisting of *Pinguiococcus pyrenoidosus*, *Aphanocapsa* sp., *Biddulphia aurita*, *Emiliania huxleyi*, *Nitzschia alba*, *Prymnesium parvum*, and *Skeletonema costatum*.

Also contemplated is a substantially pure culture comprising a growth medium; and a composition comprising:

(a) *Nannochloropsis* strain LARB-AZ 0202.0 deposited at ATCC Deposit Number PTA-11048;

(b) a *Nannochloropsis* strain LARB-AZ 0202.2 deposited at ATCC Deposit Number PTA-11049 or *Nannochloropsis* strain LARB-AZ 0202.3 deposited at ATCC Deposit Number PTA-11050, or a combination of LARB-AZ 0202.2 and LARB-AZ 0202.3;

(c) a *Nannochloropsis* strain LARB-AZ 0202.0 deposited at ATCC Deposit Number PTA-11048 and further comprises a *Nannochloropsis* strain LARB-AZ 0202.2 deposited at ATCC Deposit Number PTA-11049 or *Nannochloropsis* strain LARB-AZ 0202.3 deposited at ATCC Deposit Number PTA-11050, or a combination of LARB-AZ 0202.2 and LARB-AZ 0202.3

(d) any of the compositions in (a) through (c) further comprising two or more isolated algal strains selected from the group consisting of *Pinguiococcus pyrenoidosus*, *Aphanocapsa* sp., *Biddulphia aurita*, *Crypthecodinium* sp., *Emiliania huxleyi*, *Nitzschia alba*, *Prymnesium parvum*, *Skeletonema costatum*, and *Trichodesmium erythraeum*, wherein the *Nannochloropsis* strain LARB-AZ 0202.0 or a mutant thereof and the two or more algal strains make up at least 90% of the algae present in the composition. For example, the two or more isolated algal strains comprise one or both of *Crypthecodinium* sp. and *Trichodesmium erythraeum*. In other embodiments, the two or more isolated algal strains further comprise an algal strain selected from the group consisting of *Pinguiococcus pyrenoidosus*, *Aphanocapsa* sp., *Biddulphia aurita*, *Emiliania huxleyi*, *Nitzschia alba*, *Prymnesium parvum*, and *Skeletonema costatum*.

Also contemplated herein is a hydrocarbon fraction, produced by the methods described herein. Also contemplated is an isolated medium chain hydrocarbon fraction produced by the methods described herein.

In particular, the present invention contemplates kerosene produced by the methods described herein. In specific embodiments, the *Nannochloropsis* strain LARB-AZ 0202.0 or a mutant thereof is grown in a cell culture that comprises 1.5 g/L NaNO$_3$ and at high light intensity of 350 µmol photons m$^{-1}$ s$^{-1}$, and low initial N2 gas concentration of the cell culture of 0.01 g/L.

The invention further contemplates isolated *Nannochloropsis* strain wherein said *Nannochloropsis* strain comprise a sequence that is at least 99% identical to any of the sequences set forth in SEQ ID NO: 1, SEQ ID NO:2 or SEQ ID NO:3.

Embodiments of the instant invention include methods for producing algal medium chain length fatty acids or hydrocarbons, comprising culturing a first algal strain wherein the first algal strain produces a first medium chain length fatty acid subset wherein at least about 50% of the fatty acids in the subset are of a chain length of C16, wherein the culturing is conducted under conditions suitable to promote the production of the first medium chain length fatty acid subset; and extracting oil from the first algal strain to produce a medium chain length combination; wherein the medium chain length combination comprises carbon chain length C10, C12, C14 and C16 fatty acids or hydrocarbons, wherein said oil is enriched for C16 fatty acids such that greater than about 50% of the fatty acids in said oil are C16 fatty acids. In some embodiments of the invention, at least about 60% of the fatty acids in the subset are of a chain length of C16. In others, the oil is enriched for C16 fatty acids such that greater than about 60% of the fatty acids in said oil are C16 fatty acids.

In some embodiments of the invention, the first algal strain is selected from the group consisting of *Nannochloropsis* strain LARB-AZ 0202.0 (ATCC Deposit Number PTA-11048), LARB-AZ 0202.2 (ATCC Deposit Number PTA 11049), LARB-AZ 0202.3 (ATCC Deposit Number PTA-11050), *Nannochloropsis* sp., *Pinguiococcus pyrenoidosus, Aphanocapsa* sp., *Biddulphia aurita, Crypthecodinium* sp., *Emiliania huxleyi, Nitzschia alba, Prymnesiumparvum, Skeletonema costatum*, and *Trichodesmium erythraeum*.

In yet other embodiments, the method further comprises a second algal strain selected from the group consisting of *Nannochloropsis* strain LARB-AZ 0202.0 (ATCC Deposit Number PTA-11048), LARB-AZ 0202.2 (ATCC Deposit Number PTA 11049), LARB-AZ 0202.3 (ATCC Deposit Number PTA-11050), *Nannochloropsis* sp., *Pinguiococcus pyrenoidosus, Aphanocapsa* sp., *Biddulphia aurita, Crypthecodinium* sp., *Emiliania huxleyi, Nitzschia alba, Prymnesiumparvum, Skeletonema costatum*, and *Trichodesmium erythraeum*.

In still other embodiments, the method includes converting oil extracted from the first algal strain into a hydrocarbon fraction and refining the hydrocarbon fraction to produce one or more sub-fractions enriched in medium chain length hydrocarbons, enriched in carbon chain lengths C8, C10, C12, C14, or C16.

Further embodiments of the invention also comprise culturing one or more further algal strains that produce a second medium chain length fatty acid subset wherein at least about 20% of the fatty acids in said subset are medium chain length fatty acids, wherein the culturing is conducted under conditions suitable to promote the production of the second medium chain length fatty acid subset. In still others, the method includes a first algal strain and one or more further algal strains cultured as separate cultures, or cultured together as a co-culture.

In some embodiments, the method further comprises generating one or more sub-fractions enriched in carbon chain length C16. In still other embodiments, the methods further comprise producing kerosene from the one or more fractions.

The method of any one of claims 3-8 wherein the one or more further algal strains comprises at least a second algal strain and a third algal strain that is different from said first and second algal strains and selected from the group consisting of *Nannochloropsis* strain LARB-AZ 0202.0 (ATCC Deposit Number PTA-11048), LARB-AZ 0202.2 (ATCC Deposit Number PTA 11049), LARB-AZ 0202.3 (ATCC Deposit Number PTA-11050), *Nannochloropsis* sp., *Pinguiococcus pyrenoidosus, Aphanocapsa* sp., *Biddulphia aurita, Crypthecodinium* sp., *Emiliania huxleyi, Nitzschia alba, Prymnesiumparvum, Skeletonema costatum*, and *Trichodesmium erythraeum*.

Other embodiments of the instant invention include methods for producing algal medium chain length fatty acids or hydrocarbons, comprising culturing one or more of *Nannochloropsis* strain LARB-AZ 0202.0 (ATCC Deposit Number PTA-11048), LARB-AZ 0202.2 (ATCC Deposit Number PTA 11049), LARB-AZ 0202.3 (ATCC Deposit Number PTA-11050), under conditions suitable to promote the production of a first medium chain length fatty acid subset comprising at least about 50% C16 fatty acids or hydrocarbons, culturing one or more further algal strains under conditions suitable to promote the production of a second medium chain length fatty acid subset comprising at least about 50% C10 or C14 chain length fatty acids or hydrocarbons, culturing one or more further algal strains under conditions suitable to promote the production of a second medium chain length fatty acid subset comprising at least about 50% C10 or C12 chain length fatty acids or hydrocarbons, and extracting oil from the cultured *Nannochloropsis* strain LARB-AZ 0202.0 or a mutant thereof and the one or more further algal strains to produce a medium chain length combination, wherein the medium chain length combination comprises carbon chain length C16, C14 and one or more of C10 and C12 fatty acids or hydrocarbons.

Some embodiments further comprise converting the medium chain length combination into a hydrocarbon fraction and further comprising refining the hydrocarbon fraction to produce one or more fractions enriched in medium chain length hydrocarbons, wherein the one or more fractions comprises one or more fractions enriched in carbon chain length C10, C12, C14, and C16 hydrocarbons. In still other embodiments, the mutant of *Nannochloropsis* strain LRB-AZ 20202.0 is a LRB-AZ 0202.2 deposited at ATCC Deposit Number PTA-11049 or a LRB-AZ 0202.3 deposited at ATCC Deposit Number PTA-11050.

In other embodiments, the medium chain length combination is prepared by combining oil extracted from the *Nannochloropsis* strain LRB-AZ 0202.0 or a mutant thereof and the one or more further algal strains after oil extraction or by extracting oil from a culture comprising both the *Nannochloropsis* strain LRB-AZ 0202.0 or a mutant thereof and the one or more further algal strains. In still other embodiments, the method further comprises a second algal strain and a third algal strain, wherein the third algal strain is selected from the group consisting of *Nannochloropsis* strain LARB-AZ 0202.0 (ATCC Deposit Number PTA-11048), LARB-AZ 0202.2 (ATCC Deposit Number PTA 11049), LARB-AZ 0202.3 (ATCC Deposit Number PTA-11050), *Nannochloropsis* sp., *Pinguiococcus pyrenoidosus, Aphanocapsa* sp., *Biddulphia aurita, Crypthecodinium* sp., *Emiliania huxleyi, Nitzschia alba, Prymnesiumparvum, Skeletonema costatum*, and *Trichodesmium erythraeum*.

In still other embodiments, the methods further comprise co-culturing a second algal strain which produces a second medium chain fatty acid subset which is different from the first. In some embodiments, the second medium chain fatty acid subset comprises C8, C10, C12, or C14 fatty acids. In yet other embodiments, at least one medium chain length fatty acid subset comprises at least about 5% of total dry cell weight.

In still other embodiments, at least one medium chain fatty acid subset is isolated from *Nannochloropsis* sp. or a mutant thereof. Still other embodiments further comprise converting one or more medium chain length fatty acid subsets into one or more hydrocarbon fractions, comprising a deoxygenation/hydroxylation step. In some embodiments, the hydrocarbon fraction comprises at least about 50% C16 chain length hydrocarbons. In still others, the embodiments further comprise blending the one or more hydrocarbon fractions to generate refined oils enriched with two or more hydrocarbons of specific carbon chain lengths selected from the group consisting of C8, C10, C12, C14, and C16. In some embodiments of the invention, the two or more hydrocarbons of specific chain lengths are C10 and C12. In still other embodiments, the two or more hydrocarbons of specific chain lengths are C12 and C14. In yet others, the two or more hydrocarbons of specific chain lengths are C10 and C14. In further embodiments, the two or more hydrocarbons of specific chain lengths are C8 and C10. In still further aspects, the two or more hydrocarbons of specific chain lengths are C10 and C16.

In some embodiments of the invention, the refined oil is kerosene. In some embodiments, the kerosene comprises a distribution of hydrocarbons in C8-C16 range. In still others, the kerosene comprises a distribution of hydrocarbons in the C10-C16, C8-C14, or C10-C14 range.

Some embodiments of the invention are compositions comprising a *Nannochloropsis* strain LRB-AZ 0202.2 deposited at ATCC Deposit Number PTA-11049 or *Nannochloropsis* strain LRB-AZ 0202.3 deposited at ATCC Deposit Number PTA-11050, or a combination of LRB-AZ 0202.2 and LRB-AZ 0202.3.

Embodiments of the invention also include methods wherein at least one algal medium chain fatty acid subset is isolated from any one of the organisms selected from the group consisting of *Nannochloropsis* strain LARB-AZ 0202.0 (ATCC Deposit Number PTA-11048), LARB-AZ 0202.2 (ATCC Deposit Number PTA 11049), LARB-AZ 0202.3 (ATCC Deposit Number PTA-11050), *Nannochloropsis* sp., *Pinguiococcus pyrenoidosus*, *Aphanocapsa* sp., *Biddulphia aurita*, *Crypthecodinium* sp., *Emiliania huxleyi*, *Nitzschia alba*, *Prymnesiumparvum*, *Skeletonema costatum*, and *Trichodesmium erythraeum*.

Some embodiments of the methods disclosed herein comprise growing algal cells under culturing conditions comprising 1.5 g/L $NaNO_3$ and at a light intensity of about 350 µmol photons $m^{-2}$ $s^{-1}$, and initial $N_2$ gas concentration of the cell culture of about 0.01 g/L.

Some embodiments of the invention include a hydrocarbon fraction produced by the methods disclosed herein. Others include an isolated medium chain length hydrocarbon fraction produced by the methods disclosed herein. Still others include kerosene produced by the methods disclosed herein.

BRIEF DESCRIPTION OF THE DRAWINGS

FIG. 17: ITS sequence of *Nannochloropsis* sp. LARB-AZ 0202.0 (SEQ ID NO:1).

FIG. 18: ITS sequence of *Nannochloropsis* sp. LARB-AZ 0202.2 (SEQ ID NO:2).

FIG. 19: ITS sequence of *Nannochloropsis* sp. LARB-AZ 0202.3 (SEQ ID NO:3).

FIG. 20: Phylogenetic tree of *Nannochloropsis* sp. LARB-AZ 0202.0 and mutants LARB-AZ 0202.2 and LARB-AZ 0202.3.

DETAILED DESCRIPTION

Figure 1:
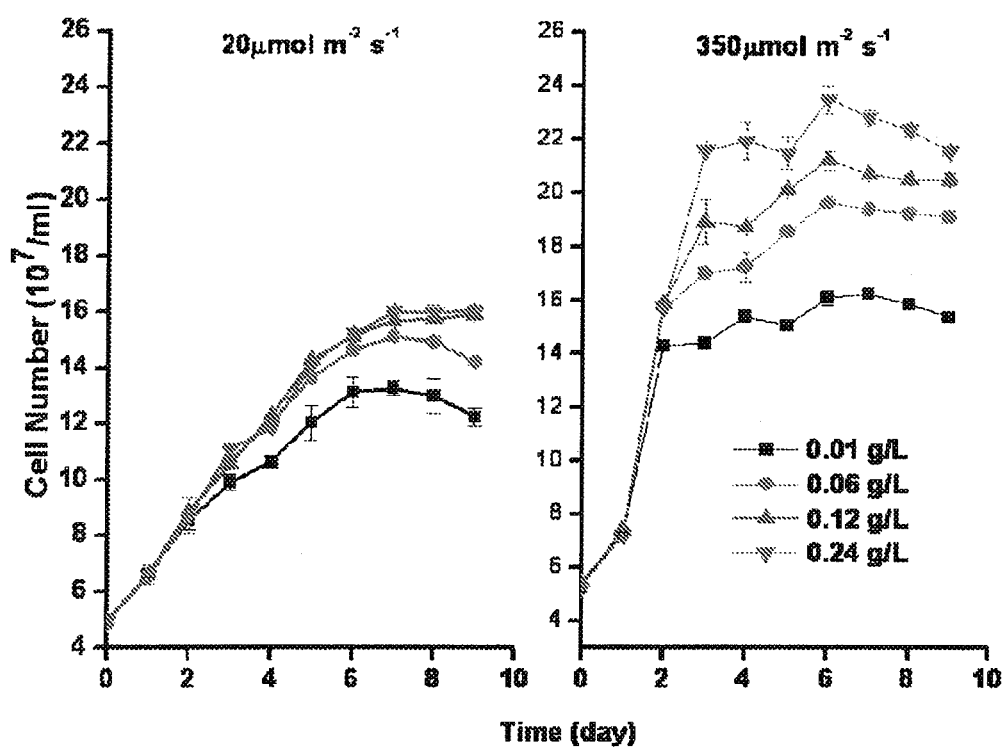
FIG. 1: The effect of light intensities and initial nitrogen concentrations on growth of LARB-AZ 0202.0 grown in the glass columns (5 cm in diameter) containing 600 ml of basal F/2 culture medium. The culture temperature was maintained at 25° C. and cultures were agitated by bubbling of compressed air containing 1~2% CO2 through a glass capillary tube inserted into the bottom of the glass column.

Previous efforts to produce algal oil fractions enriched in medium chain length fatty acids used a cracking process to break long chain fatty acids/esters into shorter ones, followed by further processing. The methods of the present invention do not require such a cracking process, but instead rely on the use of algae that endogenously produce medium chain length fatty acids and not hydrocarbons. As a result, the methods of the invention using this algal strain allow isolation of algal fatty acids and processing into a hydrocarbon fraction using, for example, a deoxygenation step. In particular, the present inventors have identified a specific strain of *Nannochloropsis* (LARB-AZ 0202.0) that comprises a greater than 50% C16 fatty acid content. Indeed, the *Nannochloropsis* strain is one which comprises approximately 68% C16 fatty acids which is greater than any other *Nannochloropsis* algal strain identified to date.

The *Nannochloropsis* LARB-A 0202.0 can be distinguished from other *Nannochloropsis* strains in that it has an ITS sequence that comprises the sequence of SEQ ID NO:1. The *Nannochloropsis* LARB-A 0202.2 can be distinguished from other *Nannochloropsis* strains in that it has a ITS sequence that comprises the sequence of SEQ ID NO:2. The *Nannochloropsis* LARB-A 0202.3 can be distinguished from other *Nannochloropsis* strains in that it has a ITS sequence that comprises the sequence of SEQ ID NO:3. Thus, the present invention relates to novel *Nannochloropsis* LARB-A 0202.0 which is deposited at ATCC Deposit Number PTA-11048, mutants thereof deposited at ATCC Deposit Number PTA-11049 and ATCC Deposit Number PTA-11049, as well as *Nannochloropsis* strains that comprise a ITS sequence that comprises a sequence that is at least 99%, preferably at least 99.4%, preferably at least 99.5%, or 99.6% or 99.7% or 99.8% identical to the sequence set forth in SEQ ID NO:1, SEQ ID NO:2 or SEQ ID NO:3.

The methods of the invention can produce, for example, more kerosene-based jet fuel than "common" algal oils which are enriched with a mixture of long chain fatty acids (C16 to C22) with a given amount of algal feedstock. As such, the invention can beneficially reduce capital and operational costs associated with the oil cracking and separation processes.

Algal oil from *Nannochloropsis* LARB-AZ 0202.0 (and the mutants thereof described herein) enriched in C16 chain length fatty acids can be used for various purposes, including but not limited to production of algal-based kerosene substitutes, high quality detergents, and research reagents (for example, isolated hydrocarbon fractions of a single chain length for use as standards that can be optionally labeled for research use).

As used herein, the phrase "medium chain length fatty acids" refers to fatty acids and esters thereof that range in carbon chain length from C8 to C16. The *Nannochloropsis* strains of the present invention may be used in combination with two or more other algal strains (i.e.: 2, 3, 4, 5, or more algal strains) to produce and accumulate large quantities of medium chain length fatty acids. "Large quantities" means that 20% or more of total fatty acids produced by the algal strain are medium-chain length fatty acids. In a further embodiment, the two or more algal strains produce and accumulate at least 25% of the fatty acids produced as medium chain length fatty acids; more preferably, at least 30%, 35%, 40%, 45%, 50%, 55%, or more. Those of skill in the art will understand that while the algal strains employed produce medium-chain fatty acids, they may also produce other chain length fatty acids.

As used herein, the term "algae" or "algal strain" includes both microalgae and cyanobacteria. In one embodiment, the algae are eukaryotic microalgae.

"Suitable conditions" for culturing algae are well known to those of skill in the art, and include appropriate light conditions (to promote photosynthetic growth), growth media (nutrients, pH, etc.), and CO2 supply. The volume of growth medium can be any volume suitable for cultivation of the algae for methods of the invention. Any suitable nutrient supply can be used. Such nutrient supplies can include (or can supplemented by) wastewater or waste gases. In these embodiments, the methods further provide waste remediation benefits. For example, nutrient-contaminated water or wastewater (e.g., industrial wastewater, agricultural wastewater domestic wastewater, contaminated groundwater and surface water), or waste gases emitted from power generators burning natural gas or biogas, and flue gas emissions from fossil fuel fired power plants can be used as part of the growth medium. In these embodiments, the algae can be first cultivated in a primary growth medium, followed by addition of wastewater and/or waste gas. Alternatively, the algae can be cultivated solely in the waste stream source. When a particular nutrient or element is added into the culture medium, it will be taken up and assimilated by the algae. Typically, waste water is added to the culture medium at a desired rate. This water, being supplied from the waste water source, contains additional nutrients, such as phosphates, and/or trace elements (such as iron, zinc), which supplement the growth of the algae. In one embodiment, if the waste water being treated contains sufficient nutrients to sustain the microalgal growth, it may be possible to use less of the growth medium. As the waste water becomes cleaner due to algal treatment, the amount of growth medium can be increased. The major factors affecting waste-stream feeding rate include: 1) algal growth rate, 2) light intensity, 4) culture temperature, 5) initial nutrient concentrations in wastewater; 5) the specific uptake rate of certain nutrients; 6) design and performance of a specific bioreactor and 7) specific maintenance protocols.

Growth of the algae can be in any type of system or photobioreactor. As used herein, a "photobioreactor" is an industrial-scale culture vessel made of transparent clear materials (e.g., glass, acrylic, polycarbonate, PVC, etc) in which algae grow and proliferate. For use in this aspect of the invention, any type of system or photobioreactor can be used, including but not limited to open raceways (i.e. shallow ponds (water level ca. 15 to 30 cm high) each covering an area of 1000 to 5000 m$^2$ constructed as a loop in which the culture is circulated by a paddle-wheel, closed systems, i.e. photobioreactors made of transparent tubes or containers in which the culture is mixed by either a pump or air bubbling, tubular photobioreactors and flat plate-type photobioreactors.

As used herein, "conditions suitable to promote production" means that the conditions employed result in algal production of medium chain length fatty acids equal to at least 5% of total dry cell weight, and preferably 10%, 15%, 20%, 25%, or more.

The methods of the invention comprise extracting oil (i.e.: total fatty acids) from algae. Any suitable process for extracting oil from the algae can be used, including but not limited to solvent extraction and supercritical fluid extraction. Initially, algae are harvested from liquid culture in the photobioreactor using a suitable harvesting method (such as centrifugation, dissolved air floatation, membrane filtration, polymer-assisted flocculation, etc., singularly or in combination). The harvested algae can then be dried, if desired, using any suitable technique (such as sun-drying, drum-drying, freeze drying, or spray-drying) The resulting dried algae can be in any useful form, including but not limited to a form of algal flour.

As used herein, a "medium chain length fatty acid subset" is the set of medium chain length fatty acids produced by a given algal strain. Thus, culturing an algal strain that can produce large quantities of a medium chain length fatty acid subset under conditions suitable to promote production of the medium chain fatty acid subset, results in production of a medium chain length fatty acid subset that comprises at least 5% of total dry cell weight. The subset may comprise medium chain length fatty acids of any specific chain length or combination of chain lengths. The methods comprise use of a first algal strain that is a *Nannochloropsis* LARB-AZ 0202.0 strain or a mutant thereof that produces a first medium chain fatty acid subset which comprises at least 50% C16 fatty acids as compared to the total fatty acids produced by the strain.

The methods may use the *Nannochloropsis* LARB-AZ 0202.0 strain of the invention alone, or in combination with one or more mutants of *Nannochloropsis* LARB-AZ 0202.0. In further embodiments, the methods may use *Nannochloropsis* LARB-AZ 0202.0 strain of the invention and/or one or more mutants of *Nannochloropsis* LARB-AZ 0202.0 strain of the invention in combination with one or more further algal strains to produce a second or further medium chain fatty acid. Thus, where two algal strains are used, it is contemplated that the first strain is a *Nannochloropsis* strain as described herein and the second strain is another algal strain that produces a high level of one or more medium chain length fatty acid subset comprising C10, C12, and C14 fatty acids; likewise, where three algal strains are used the methods comprise production of three medium chain fatty acid subsets (where one of the three algal strains individually produce C16 and the other algal strains produce other medium chain length fatty acid subset comprising C10, C12, and C14 fatty acids), and so on.

As used herein a "medium chain length combination" is a combined medium-chain length product (fatty acids or hydrocarbons) from the first algal strain that is a *Nannochloropsis* LARB-AZ 0202.0 wild type (deposited with ATCC under deposit number PTA-11048 on Jun. 15, 2010) or a mutant thereof (e.g., *Nannochloropsis* LARB-AZ 0202.2 deposited with ATCC under deposit number PTA-11049 on Jun. 15, 2010 or *Nannochloropsis* LARB-AZ 0202.3 deposited with ATCC under deposit number PTA-11050 on Jun. 15, 2010) and is responsible for the production of the bulk of C16 fatty acids and hydrocarbons and one or more other algal strains that are responsible for the production of a medium chain length combination that comprises carbon chain length C10, C12, and C14 fatty acids or hydrocarbons. The medium chain length combination may comprise either medium chain length fatty acids or medium chain length hydrocarbons, depending on the stage of processing.

In one embodiment, the first algal strain that is a *Nannochloropsis* LARB-AZ 0202.0 strain or mutant thereof and the one or more algal strains are co-cultured; in this case a medium chain length combination comprising medium chain length fatty acids is obtained upon oil extraction; if the medium chain length combination is then further processed to produce a hydrocarbon fraction (see below), then the medium chain length combination will comprise medium chain length hydrocarbons after hydrocarbon fractionation. In another embodiment, the first (i.e., the *Nannochloropsis* LARB-AZ 0202.0 strain of the invention or a mutant thereof) algal strain and the one or more further algal strains are cultured separately; in this embodiment, the medium chain length combination is obtained sometime after oil extraction. For example, the first and second (or further) subsets can be combined immediately after oil extraction (resulting in a medium chain length combination comprising medium chain length fatty acids); or after other steps, such as after hydrocarbon fractionation, or after production of one or more fractions enriched in medium chain length hydrocarbons (see below), either of which results in a medium chain length combination comprising medium chain length hydrocarbons. As will be apparent to one of skill in the art, if three or more algal strains are used, they could all be co-cultured, or a subset could be co-cultured while other algal strains are cultured separately, and thus the combination of their medium chain length fatty acid subset or medium chain length hydrocarbons may comprise multiple combination events.

Oil extraction from algae can be accompanied by extraction of other algal biomass that is separated from the oil during the extraction process. Thus, in another embodiment, the methods of the invention further comprise isolating algal biomass. Such biomass can include, but is not limited to, bulk products (useful, for example, for animal feed and biofertilizer); ethanol and methane (requires subsequent fermentation; useful, for example, in energy production); and specialty products, including but not limited to pigments (chlorophyll), polymers, carotenoids (e.g., beta-carotene, zeaxanthin, lutein, and astaxanthin), and polyunsaturated fatty acids.

The methods of the invention further comprise converting oil extracted from the first algal strain i.e., *Nannochloropsis* LARB-AZ 0202.0 strain or mutants thereof or combinations of the *Nannochloropsis* LARB-AZ 0202.0 strain and one or more mutants thereof. Optionally, the methods may further comprise converting oil extracted from one or more further algal strains into a hydrocarbon fraction (i.e.: conversion of fatty acids into hydrocarbons). Any suitable process for converting algal fatty acids into hydrocarbons can be used, including but not limited to a deoxygenation/hydroxylation process, such as by chemical catalysis or hydrogen loading. A medium chain length combination prepared following hydrocarbon fractionation comprises medium chain length hydrocarbons. Such a medium chain length combination can be produced in whole or in part (by combination of hydrocarbon fractions produced from less than all of the algal strains employed) after hydrocarbon fractionation, or hydrocarbon fractionation can be performed separately on oil extracted from each algal strain. At least 30% of the hydrocarbons present in the hydrocarbon fraction are medium chain length hydrocarbons; in further embodiments, at least 35%, 40%, 45%, 50%, 55%, or more of the hydrocarbons present in the hydrocarbon fraction are medium chain length hydrocarbons.

As will be apparent to those of skill in the art, byproducts of hydrocarbon conversion, such as lighter fractions of hydrocarbons (e.g., C1-C6) and/or glycerol (glycerin), can also be obtained during hydrocarbon fractionation. Thus in a further embodiment, the methods further comprises isolating short-chain hydrocarbon molecules (C1-C6) and/or glycerol. The short chain hydrocarbons can be used, for example, to make tail gas or gasoline. Glycerol has many uses, including but not limited to use in pharmaceutical products (used as/in, for example, lubricants, humectants, expectorants, cough syrups, etc.), personal care products (used as/in, for example, emollients, lubricants, humectants, solvents, toothpastes, mouthwashes, skin care products, soap, etc.) and food/beverage products (sweetener, filler, etc.).

In a further embodiment, the methods comprise refining the hydrocarbon fraction to produce one or more fractions enriched in medium chain length hydrocarbons, wherein the one or more fractions comprise one or more fractions enriched in C16 chain length as well as one or more fractions enriched in carbon chain length C10, C12, and/or C14 hydrocarbons. For example, a separation/refining technology separates and concentrates desirable hydrocarbon fractions from a deoxygenation process, resulting in a series of refined fractions enriched with one or more hydrocarbons of specific carbon chain lengths. A medium chain length combination prepared following refining comprises medium chain length hydrocarbons. Such a medium chain length combination can be produced in whole or in part (by combination of hydrocarbons produced from less than all of the algal strains employed) after refining, or refining can be performed separately on hydrocarbon fractions from each algal strain. The one or more fractions can comprise a single fraction that comprises the C16 chain length enriched fatty acids from the *Nannochloropsis* LARB-AZ 0202.0 wild type or mutants thereof in combination with the C10, C12, and C14 chain length hydrocarbons from the other algal strains, four separate fractions, one comprising the C16 chain length enriched hydrocarbons from the *Nannochloropsis* LARB-AZ 0202.0 wild type or mutants thereof, one comprising C10 chain length hydrocarbons, one comprising C12 chain length hydrocarbons, and one comprising C14 chain length hydrocarbons, or other variations thereof. At least 90% of the hydrocarbons present in each fraction enriched in medium chain length hydrocarbons are of the desired chain length(s) hydrocarbon; in various further embodiments at least 91%, 92%, 93%, 94%, 95%, 96%, 97%, 98%, 99%, or more of the hydrocarbons present in each fraction enriched in medium chain length hydrocarbons are of the desired chain length(s) hydrocarbon.

Any suitable refining process can be used that serves to separate and concentrate fractions enriched in medium chain length fatty acids. In various embodiments, the refining comprises vacuum distillation or molecular distillation to separate and purify medium-chain (C8-C16) fatty acid (FA) or fatty acid methyl ester (FAME) from long-chain fatty acids (C18 or longer) or FAME. Vacuum distillation has been extensively used in petroleum refining, whereas molecular distillation is a newer technology that has been proved to be effective in separating one liquid from complex liquid mixtures. The vacuum distillation is similar in principle with the conventional fractional distillation (commonly called atmospheric distillation to distinguish it from the vacuum method), except that larger-diameter columns are used in vacuum distillation to maintain comparable vapor velocities at reduced operating pressures. A vacuum of 50 to 100 millimeters of mercury absolute is produced by a vacuum pump or steam ejector. The major advantage of vacuum distillation is that it allows for distilling heavier materials at lower temperatures than those that would be required at atmospheric pressure, thus avoiding thermal cracking of the components. An extension of the distillation process, superfractionation employs smaller-diameter columns with a much larger number of trays (100 or more) and reflux ratios exceeding 5:1. With such equipment it is possible to isolate a very narrow range of components or even pure compounds. Common applications involve the separation of high-purity solvents such as isoparaffins or of individual aromatic compounds for use as petrochemicals.

Molecular distillation is characterized by short exposure of the distilled liquid to elevated temperatures, high vacuum in the distillation space, and a small distance between the condenser and evaporator. The short residence of the liquid on the evaporating cylinder, in the order of a few seconds to 1 min, is guaranteed by distributing the liquid in the form of a uniform thin film. By reducing the pressure of non-condensable gas in the evaporator to lower than 0.1 Pa, a reduction in distillation temperatures can be obtained. Molecular distillation shows promise in the separation, purification and concentration of natural products, usually composed of complex and thermally sensitive molecules. Furthermore, this process has advantages over other techniques that use solvents as the separating agent, avoiding problems with toxicity. Centrifugal and falling films are two basic types of molecular distillation units that use short exposure of the distilled liquid to the evaporating cylinder. These types of distillation units have been used to demonstrate and compare the distillation of many different compounds, such as fatty acids, including the isomers with same carbon numbers in the molecular structures (for example: this technology can be used to separate C18: 3 from C18: 2, C18: 1 or C18: 0).

The refining process results in one or more refined oils enriched in carbon chain length C16 fatty acids. The refining process may further lead to refined oils enriched with one or more medium chain length fatty acids (for example, C10, C11, C12, C13, or C14).

In another embodiment, the methods further comprise blending one or more of the medium chain length hydrocarbon fractions. Such blending can comprise any combination of medium chain length fatty acid fractions desired for a given purpose (i.e.: C10 and C12; C12 and C14; C10 and C14; C8, C10 and C16, etc.). For example, blending can result in a series of refined oils enriched with two or more hydrocarbons of specific carbon chain lengths.

In one embodiment, blending can be used to produce kerosene. As used herein, "kerosene" is a distribution of a variety of hydrocarbons in the C8-C16 range; preferably in the C10-C16, C8-C14, or C10-C14 range, and can be used, for example, in jet engine fuel (including but not limited to Jet-A, Jet-A1, Jet-B, JP-4, JP-5, JP-7, and JP-8); rocket fuel (including but not limited to RP-1); heating fuel (such as in kerosene heaters, portable stoves, and other heating sources); and to power appliances where electrical power is not otherwise available. It will be understood by those of skill in art that the kerosene can also be produced by appropriate production of medium chain length hydrocarbon fractions from the hydrocarbon fraction. In one embodiment, producing kerosene comprises combining two or more of the fractions enriched in medium chain hydrocarbons, where the resulting kerosene comprises at least 50% C16 chain length hydrocarbons extracted and prepared from the *Nannochloropsis* LARB-AZ 0202.0 strain of the present invention or mutants thereof (including *Nannochloropsis* LARB-AZ 0202.2, *Nannochloropsis* LARB-AZ 0202.3, and *Nannochloropsis* strains that comprise a ITS sequence that comprises a sequence at least 99.4% identical to the sequence of any of SEQ ID NO:1, SEQ ID NO:2 or SEQ ID NO:3) along with additional amounts of C10, C12, and C14 chain length hydrocarbons from other algal strains; in various further embodiments, at least 55%, 60%, 65%, 70%, 75%, 89%, 85%, 90%, 95%, 98% of carbon chain length C10, C12, and C14 hydrocarbons. The fractions so combined may comprise medium chain length hydrocarbons of the same type or different. In another embodiment, the kerosene may further comprise carbon chain length C16, C8 and/or C9 fatty acids each, if present, at 15% or less of the total hydrocarbon present in the kerosene; in preferred embodiments, each, if present, at less than 10%, 9%, 8%, 7%, 6%, 5%, 4%, 3%, 2% or less of the total hydrocarbon present in the kerosene.

Acceptable JP-8 surrogate fuel can thus be obtained by the blending of one or more fractions enriched in medium chain length hydrocarbons along with other additives according to the specification and qualification of petroleum derived JP-8 or other aviation fuels.

In a further embodiment the first algal strain that is a *Nannochloropsis* LARB-AZ 0202.0 or a mutant thereof is combined with one or more further algal strains are selected from the group consisting of *Pinguiococcus pyrenoidosus*, *Aphanocapsa* sp. (Kenyon, 1972), *Biddulphia aurita* (Orcutt & Patterson 1975), *Crypthecodinium* sp., *Emiliania huxleyi* (Volkman et al. 1981), *Nitzschia alba* (Tornabene et al. 1974), *Prymnesium parvum* (Lee & Loeblich 1971), *Skeletonema costatum* (Adman et al. 1964), and *Trichodesmium erythraeum* (Parker et al. 1967). The types of medium chain fatty acids produced these organisms (and thus the potential medium chain fatty acid subsets) can be found in WO/2008/036654 Table 1 and FIG. 1; based on the teachings herein, those of skill in the art will understand which algal strains to use, depending on the type of medium chain length combination desired. In specific embodiments, the algal strains are identified as follows:

| | |
|---|---|
| *Pinguiococcus pyrenoidosus* (*Pinguiophyceae*) | CCMP2078 |
| *Crypthecodinium* sp. | CCMP316 |
| *Aphanocapsa* sp.: | CCMP2524 |
| *Odontella aurita*: | CCMP145 |
| *Emiliania huxleyi*: | CCMP1742 |
| *Nitzschia alba*: | CCMP2426 |
| *Prymnesium parvum*: | CCMP1962 |
| *Skeletonema costatum*: | CCMP1281 |
| *Trichodesmium* sp.: | CCMP1985 |

All of the algal strains can be obtained from CCMP address: Provasoli-Guillard National Center for the Culture of Marine Phytoplankton, Bigelow Laboratory for Ocean Sciences, P.O. Box 475, 180 McKown Point Road, West Boothbay Harbor, Me. 04575, U.S.A.)

The present invention provides methods for producing algal medium chain length fatty acids, comprising
  (a) cultures of *Nannochloropsis* LARB-0202.0 (deposited with ATCC under deposit number PTA-11048 on Jun. 15, 2010) or mutants thereof ((*Nannochloropsis* LARB-AZ 0202.2 deposited with ATCC under deposit number PTA-11049 on Jun. 15, 2010 and *Nannochloropsis* LARB-AZ 0202.3 deposited with ATCC under deposit number PTA-11050 on Jun. 15, 2010) deposited under the Budapest Treaty Form (BP/1) with the American Type Culture Collection (ATCC), IP Licensing and Services, 10801 University Boulevard, Manassas, Va. 20110-2209, USA under conditions to maintain viability and integrity of cultures for subsequent production of medium chain length fatty acids); and
  (b) extracting oil from the cultured *Nannochloropsis* LARB-AZ 0202.0 wild type and mutants thereof (LARB-AZ 0202.2 and LARB-AZ 0202.3) wherein at least 50% of the total fatty acids in the extracted oil comprise C16 chain length fatty acids.

The inventors have discovered that *Nannochloropsis* LARB-AZ 0202.0 and mutants thereof (LARB-AZ 0202.2 and LARB-AZ 0202.3, such as the strains deposited at ATCC under deposit numbers PTA-11048, PTA-11049, and PTA-11050, respectively, on Jun. 15, 2010, are capable of producing large amounts of C16 chain length medium chain length fatty acids. Thus, the methods of the invention can be used for various purposes, including but not limited to production of algal-based kerosene substitutes, high quality detergents, and research reagents (for example, isolated hydrocarbon fractions of a single chain length for use as standards that can be optionally labeled for research use).

In a further embodiment, the methods comprise converting oil extracted from *Nannochloropsis* LARB-AZ 0202.0, and mutants thereof (LARB-AZ 0202.2, LARB-AZ 0202.3) into a hydrocarbon fraction, where hydrocarbon fraction comprises at least 50% C16 chain length hydrocarbons as isolated from the *Nannochloropsis* LARB-AZ 0202.0 wild type or mutants thereof (LARB-AZ 0202.2 and LARB-AZ 0202.3).

In another embodiment, the methods further comprise refining the hydrocarbon fraction to produce one or more fractions enriched particularly in C16 medium chain length hydrocarbons, wherein the one or more fractions comprises at least one fraction enriched in carbon chain length C16 hydrocarbons. In a further embodiment, the one or more fractions comprise at least one fraction enriched in carbon chain length C14 hydrocarbons or C18 hydrocarbons. In a further embodiment, the method further comprises blending the one or more fractions enriched in medium chain length hydrocarbons to produce, for example, kerosene. Such blending may further comprise blending with medium chain length hydrocarbon fractions derived from another algal strain, such as C14 and C16 producer such as for example *Pinguiococcus pyrenoidosus* variant CCMP 2078 and/or a producer of C10 and/or C12 chain length hydrocarbon chains (for example, those derived from *Crypthecodinium* sp. and/or *Trichodesmium erythraeum*). These methods of the invention may also comprise isolating algal biomass, and/or isolating short-chain hydrocarbon molecules and/or glycerol, as disclosed in the methods described above.

In addition, the present invention provides methods for producing algal medium chain length fatty acids or hydrocarbons, comprising
  (a) culturing *Nannochloropsis* LARB-AZ 0202.0 and mutants thereof (LARB-AZ 0202.2 and LARB-AZ 0202.3) under conditions to promote production of C16 chain length fatty acids;
  (b) culturing one or more further algal strains that can produce and accumulate large quantities of such as C14 and/or C10 and/or C12 chain length fatty acids, wherein the culturing is conducted under conditions suitable to promote production of the C14 and/or C10 and/or C12 chain length fatty acids; and
  (c) extracting oil from the cultured *Nannochloropsis* LARB-AZ 0202.0 and mutants thereof (LARB-AZ 0202.2 and LARB-AZ 0202.3) and the one or more further algal strains to produce a medium chain length combination; wherein the medium chain length combination comprises carbon chain length C16 and one or more of carbon chain length C14 and C10 and C12 fatty acids or hydrocarbons.

Such methods of the invention can be used for various purposes, including but not limited to production of algal-based kerosene substitutes, high quality detergents, and research reagents (for example, isolated hydrocarbon fractions of a single chain length for use as standards that can be optionally labeled for research use). In various embodiments, the one or more further algal strains are one or more of *Pinguiococcus pyrenoidosus, Crypthecodinium* sp. and *Trichodesmium erythraeum*. In a further embodiment, the medium chain length combination comprises carbon chain length C16 as derived from *Nannochloropsis* LARB-AZ 0202.0 or mutants thereof (LARB-AZ 0202.2 and LARB-AZ 0202.3), C10, C12, as derived from *Crypthecodinium* sp. and *Trichodesmium erythraeum* and C14 fatty acids or hydrocarbons as derived from *Pinguiococcus pyrenoidosus*. In a further embodiment, the medium chain length combination is prepared by combining oil extracted from the *Nannochloropsis* LARB-AZ 0202.0 or mutants thereof (LARB-AZ 0202.2 and LARB-AZ 0202.3) and the one or more further algal strains after oil extraction. In a further embodiment, the medium chain length combination is prepared by extracting oil from a culture comprising both the *Nannochloropsis* LARB-AZ 0202.0 or mutants thereof (LARB-AZ 0202.2, LARB-AZ 0202.3) and the one or more further algal strains (including e.g., *Pinguiococcus pyrenoidosus*).

In a further embodiment, the methods comprise converting oil extracted from *Nannochloropsis* LARB-AZ 0202.0 or mutants thereof (LARB-AZ 0202.2, LARB-AZ 0202.3) and the one or more further algal strains into a hydrocarbon fraction, where hydrocarbon fraction is as defined above. In another embodiment, the methods further comprise refining the hydrocarbon fraction to produce one or more fractions enriched in medium chain length hydrocarbons, wherein the one or more fractions comprises one or more fractions enriched in C16 carbon chain length as derived from *Nannochloropsis* LARB-AZ 0202.0 or mutants thereof (LARB-AZ 0202.2, LARB-AZ 0202.3) and one or more fractions enriched in C10, C12, and/or C14 hydrocarbons as derived from other algal strains. In a further embodiment, the one or more fractions comprise at least one fraction enriched in carbon chain length C16 hydrocarbons from *Nannochloropsis* LARB-AZ 0202.0 or a mutant thereof (LARB-AZ 0202.2, LARB-AZ 0202.3). In a further embodiment, the method further comprises blending one or more of the fractions enriched in medium chain length hydrocarbons to, for example, produce kerosene. These methods of the invention may also comprise isolating algal biomass, and/or isolating short-chain hydrocarbon molecules and/or glycerol, as described above. In a further embodiment of any of the above methods, the one or more further algal strains comprises a second algal strain and a third algal strain, wherein the third algal strain is selected from the group consisting of *Aphanocapsa* sp., *Biddulphia aurita*, *Crypthecodinium* sp., *Emiliania huxleyi*, *Nitzschia alba*, *Prymnesium parvum*, *Skeletonema costatum*, and *Trichodesmium erythraeum*.

The present invention also provides methods for producing algal medium chain length fatty acids or hydrocarbons, comprising
(a) culturing *Nannochloropsis* LARB-AZ 0202.0 or mutants thereof (such as for example LARB-AZ 0202.2, LARB-AZ 0202.3 or a *Nannochloropsis* strain derived from LARB-AZ 0202.0 that comprises a ITS sequence that is at least 99.4% identical with the sequence of SEQ ID NO: 1, SEQ ID NO:2 or SEQ ID NO:3) or a combination of *Nannochloropsis* LARB-AZ 0202.0 with one or more mutants thereof under conditions to promote production of medium chain length fatty acids, wherein the medium chain length fatty acids comprise C16 chain length fatty acids;
(b) culturing *Trichodesmium erythraeum* under conditions to promote production of medium chain length fatty acids, wherein the medium chain length fatty acids comprise C10 chain length fatty acids;
(c) culturing *Crypthecodinium* sp. under conditions to promote production of medium chain length fatty acids, wherein the medium chain length fatty acids comprise C12 chain length fatty acids;
(d) culturing *Pinguiococcus pyrenoidosus*. under conditions to promote production of medium chain length fatty acids, wherein the medium chain length fatty acids comprise C14 chain length fatty acids; and
(e) extracting oil from the cultured *Nannochloropsis* LARB-AZ 0202.0 or mutants thereof (LARB-AZ 0202.2, LARB-AZ 0202.3), *Trichodesmium erythraeum*, the *Crypthecodinium* sp. And the *Pinguiococcus pyrenoidosus* to produce a medium chain length combination; wherein the medium chain length combination comprises carbon chain length C16, C10, C12 and C14 fatty acids or hydrocarbons.

The methods of the invention can be used for various purposes, including but not limited to production of algal-based kerosene substitutes, high quality detergents, and research reagents (for example, isolated hydrocarbon fractions of a single chain length for use as standards that can be optionally labeled for research use). In one embodiment, the medium chain length combination further comprises carbon chain length C14 fatty acids or hydrocarbons. In a further embodiment, the methods further comprise (d) culturing one or more algal strains selected from the group consisting of *Pinguiococcus pyrenoidosus*, *Aphanocapsa* sp., *Biddulphia aurita*, *Emiliania huxleyi*, *Nitzschia alba*, *Prymnesium parvum*, and *Skeletonema costatum* under conditions to promote production of medium chain length fatty acids, wherein the medium chain length fatty acids comprise C14 and/or C16 chain length fatty acids; and (e) extracting oil from the cultured one or more algal strains to be included in the medium chain length combination; and wherein the medium chain length combination comprises carbon chain length C14 and/or C16 fatty acids or hydrocarbons.

In a further embodiment, the medium chain length combination is prepared by combining oil extracted from the culture *Trichodesmium erythraeum* and *Crypthecodinium* sp. after oil extraction. In another embodiment, the medium chain length combination is prepared by extracting oil from a culture comprising both the *Trichodesmium erythraeum* and *Crypthecodinium* sp. In another embodiment, the medium chain length combination is prepared by combining oil extracted from the culture *Trichodesmium erythraeum*, *Crypthecodinium* sp., and the one or more algal strains after oil extraction. In a further embodiment, the medium chain length combination is prepared by extracting oil from a culture comprising the *Trichodesmium erythraeum*, the *Crypthecodinium* sp., and the one or more algal strains. In a further embodiment, the methods further comprise converting the oil extracted from the algal strains into a hydrocarbon fraction, as defined above.

The methods may further comprise refining the hydrocarbon fraction to produce one or more fractions enriched in medium chain length hydrocarbons, wherein the one or more fractions comprises one or more fractions enriched in carbon chain length C10 and C12 hydrocarbons, and optionally C14 and/or C16 hydrocarbons. The methods may further comprise blending one or more of the fractions enriched in medium chain length hydrocarbons to, for example, produce kerosene. In various further embodiments, the methods further comprise isolating algal biomass, and/or isolating short-chain hydrocarbon molecules and/or glycerol, as discussed above.

The present invention also provides compositions comprising isolated *Nannochloropsis* strains. In one embodiment, the invention provides a composition comprising *Nannochloropsis* strain LARB-AZ 0202.0 deposited at ATCC Deposit Number PTA-11048. The invention also provides a composition comprising a *Nannochloropsis* strain LARB-AZ 0202.2 deposited at ATCC Deposit Number PTA-11049 or *Nannochloropsis* strain LARB-AZ 0202.3 deposited at ATCC Deposit Number PTA-11050, or a combination of LARB-AZ 0202.2 and LARB-AZ 0202.3. In addition, the invention also provides a composition comprising *Nannochloropsis* strain LARB-AZ 0202.0 deposited at ATCC Deposit Number PTA-11048 and a *Nannochloropsis* strain LARB-AZ 0202.2 deposited at ATCC Deposit Number PTA-11049 or *Nannochloropsis* strain LARB-AZ 0202.3 deposited at ATCC Deposit Number PTA-11050, or a combination of LARB-AZ 0202.2 and LARB-AZ 0202.3.

The present invention further provides a composition that combines the *Nannochloropsis* strains of the invention with other algal strains. For example, the present invention further provides a composition comprising two or more isolated algal strains selected from the group consisting of *Nannochloropsis* LARB-AZ 0202.0 or mutants thereof (such as e.g., LARB-AZ 0202.2, LARB-AZ 0202.3), *Pinguiococcus pyrenoidosus*, *Aphanocapsa* sp., *Biddulphia aurita*, *Crypthecodinium* sp., *Emiliania huxleyi*, *Nitzschia alba*, *Prymnesium parvum*, *Skeletonema costatum*, and *Trichodesmium erythraeum*, wherein the two or more algal strains make up at least 90% of the algae present in the composition. In further embodiments, at least 95%, 98%, or 99% of the algae present in the composition are of the recited algal type. The isolated algal composition can be cultured or stored in solution, frozen, dried, or on solid agar plates. Alternatively, the compositions may comprise harvested algal compositions (wet or dried) in, for example, the form of an algal flour. In specific embodiments, the algal strains are identified as follows:

| | |
|---|---|
| *Pinguiococcus pyrenoidosus* (*Pinguiophyceae*): | CCMP2078 |
| *Crypthecodinium* sp.: | CCMP316 |
| *Aphanocapsa* sp.: | CCMP2524 |
| *Odontella aurita*: | CCMP145 |
| *Emiliania huxleyi*: | CCMP1742 |
| *Nitzschia alba*: | CCMP2426 |
| *Prymnesium parvum*: | CCMP1962 |
| *Skeletonema costatum*: | CCMP1281 |
| *Trichodesmium* sp.: | CCMP1985 |

The above algal strains can be obtained from CCMP address: Provasoli-Guillard National Center for the Culture of Marine Phytoplankton, Bigelow Laboratory for Ocean Sciences, P.O. Box 475, 180 McKown Point Road, West Boothbay Harbor, Me. 04575, U.S.A.)

The algal compositions of invention can be used, for example, in the methods of the invention for the production of medium chain length fatty acids and hydrocarbons therefrom. In one embodiment, the composition comprises three or more isolated algal species selected from the group. In a further embodiment, the two or more isolated algal strains comprise *Nannochloropsis* LARB-AZ 0202.0 (ATCC deposit no. PTA-11048) or mutants thereof (e.g., LARB-AZ 0202.2 ATCC deposit no. PTA-11049, and LARB-AZ 0202.3 ATCC deposit no. PTA-11050). In a further embodiment, the two or more isolated strains further comprise *Pinguiococcus pyrenoidosus*. In a still further embodiment, the two or more isolated algal strains comprise one or both of *Crypthecodinium* sp. and *Trichodesmium erythraeum*.

In addition, the present invention provides a substantially pure culture comprising
  (a) growth medium; and
  (b) the composition of mixture of isolated algal strains as described above.

As used herein, the term "growth medium" refers to any suitable medium for cultivating algae of the present invention. The algae of the invention can grow photosynthetically on $CO_2$ and sunlight, plus a minimum amount of nutrients. The volume of growth medium can be any volume suitable for cultivation of the algae for any purpose, whether for standard laboratory cultivation, to large scale cultivation for use in, for example, medium chain fatty acid production. Suitable algal growth medium can be any such medium, including but not limited to BG-11 growth medium (see, for example, Rippka, 1979); culturing temperatures of between 10° and 38° C. are used; in other embodiments, temperature ranges between 15° and 30° are used. Similarly, light intensity between 20 $\mu$mol photons $m^{-2}$ $s^{-1}$ to 1000 $\mu$mol photons $m^{-2}$ $s^{-1}$ is used; in various embodiments, the range may be 100 $\mu$mol photons $m^{-2}$ $s^{-1}$ to 500 $\mu$mol photons $m^{-2}$ $s^{-1}$ or 150 $\mu$mol photons $m^{-2}$ $s^{-1}$ to 250 $\mu$mol photons $m^{-2}$ $s^{-1}$. Further, aeration is carried out with between 0% and 20% $CO_2$; in various embodiments, aeration is carried out with between 0.5% and 10% $CO_2$, 0.5% to 5% $CO_2$, or 0.5% and 2% $CO_2$.

For maintenance and storage purposes, the compositions of the invention may be maintained in standard artificial growth medium. For regular maintenance purposes, the compositions can be kept in liquid cultures or solid agar plates under either continuous illumination or a light/dark cycle of moderate ranges of light intensities (10 to 40 $\mu$mol $m^{-2}$ $s^{-1}$) and temperatures (18° C. to 25° C.). The culture Ph may vary from pH 6.5 to pH 9.5. No CO2 enrichment is required for maintenance of the compositions. In various non-limiting examples, the temperature of culture medium in growth tanks is preferably maintained at from about 10° C. to about 38° C., in further embodiments, between about 20° C. to about 30° C. In various embodiments, the growth medium useful for culturing the compositions of the present invention comprises wastewater or waste gases, as discussed above.

The present invention further provides an algal-derived hydrocarbon fraction. In one embodiment, the algal-derived hydrocarbon fraction is produced by the methods described herein above. Preferably, at least 30% of the hydrocarbons present in the hydrocarbon fraction are medium chain length hydrocarbons; in further embodiments, at least 35%, 40%, 45%, 50%, 55%, or more of the hydrocarbons present in the hydrocarbon fraction are medium chain length hydrocarbons. More preferably, at least 90% of the hydrocarbons present in each fraction enriched in medium chain length hydrocarbons are of the desired chain length(s) hydrocarbon; in various further embodiments at least 91%, 92%, 93%, 94%, 95%, 96%, 97%, 98%, 99%, or more of the hydrocarbons present in each fraction enriched in medium chain length hydrocarbons are of the desired chain length(s) hydrocarbon.

In addition, the present invention provides algal-derived kerosene. In one embodiment, algal-derived kerosene is produced from the fatty acids and hydrocarbons that are produced by the methods described above. In particular, producing kerosene may comprise combining two or more of the fractions enriched in medium chain hydrocarbons, where the resulting kerosene comprises at least 50% C16 hydrocarbons derived from *Nannochloropsis* LARB-AZ 0202.0 or mutants thereof (LARB-AZ 0202.2, LARB-AZ 0202.3) in combination with C10, C12, and C14 chain length hydrocarbons; in various further embodiments, at least 55%, 60%, 65%, 70%, 75%, 89%, 85%, 90%, 95%, 98% of carbon chain length C10, C12, and C14 hydrocarbons. The fractions so combined may comprise medium chain length hydrocarbons of the same type or different. In another embodiment, the kerosene may further comprise carbon chain length C16, C8 and/or C9 fatty acids each, if present, at 15% or less of the total hydrocarbon present in the kerosene; in preferred embodiments, each, if present, at less than 10%, 9%, 8%, 7%, 6%, 5%, 4%, 3%, 2% or less of the total hydrocarbon present in the kerosene.

EXEMPLARY EMBODIMENTS

Example 1

A general process diagram of the proposed algae-based jet fuel production technology is shown in FIG. 14.

In various non-limiting examples, the following processes can be carried out in conjunction with algae-based medium chain length fatty acid production:
  Production of algal feedstock using a number of selected algal species grown in one or more photobioreactors of same or different designs. Each selected algal species will produce large quantities of oil enriched with one or more medium-chain length fatty acids/esters.
  Oil-rich cells are harvested and dried in a form of algal flour.
  Algal flour is subjected to solvent extraction using a chemical extraction method. A supercritical liquid extraction method can also be employed as an alternative.
  Resulting algal oil is subjected to a deoxygenating/hydroxylation process to convert algal oil to hydrocarbons.

A separation/refining technology separates and concentrates desirable hydrocarbon fractions from the deoxygenation process. As a result, a series of refined oils enriched with one or more hydrocarbons of specific carbon chain lengths will be produced.

Acceptable JP-8 surrogate fuel is obtained by the blending of several refined algal oils along with other additives according to the specification and qualification of petroleum derived JP-8 or other aviation fuels.

As a by-product from algal oil extraction, algal biomass residues are prepared and used as bulk material in, for example, protein-rich animal feed or polysaccharide-rich biopolymers and fertilizer. Some specialty products such as high-value carotenoids (e.g., beta-carotene, zeaxanthin, lutein, and astaxanthin) can also be extracted and separated from selected algal strains.

High carbohydrate-containing biomass residues from oil extraction process can also be obtained and used a substrate for fermentation or anaerobic digestion to produce ethanol and/or methane, which in turn can be used to generate electricity/energy necessary for algal mass culture and oil processing/refinery processes. Remaining undigested biomass residues can be incinerated for additional heat and electricity. The generation of CO2 from anaerobic digestion and incineration processes can be recycled back into the photobioreactor to be used by the algae, resulting in zero net CO2 emissions.

The methods of the invention employ algae for medium chain fatty acid extraction and conversion into hydrocarbons, thus minimizing or eliminating the need to use cracking for hydrocarbon production, thus greatly reducing costs and energy consumption. Furthermore, resulting short-chain hydrocarbon molecules can be isolated as by-products of the methods to make tail gas or gasoline.

Example 2

The inventors have performed screening for medium-chain oil-producers from numerous algal species/strains isolated by and maintained in their laboratory. One of the algal strains tested is a marine alga *Nannochloropsis* LARB-AZ 0202.0 ATCC Number PTA-11048 and mutants thereof (LARB-AZ 0202.2 ATCC Number PTA-11049 and LARB-AZ 0202.3 ATCC Number PTA-11050, which have the ability to produce lipids enriched with C16 fatty acid, which can make up at least 50% to 60% of total fatty acids produced in the cell.

LARB-AZ 0202.0 is a *Nannochloropsis* strain that was originally isolated by Qiang Hu from the Red Sea near Eilat, Israel in March 2007. The algal strain was isolated using a standard agar plating approach and has been since maintained in F/2 artificial culture medium at room temperature and continuous illumination of ca. 20 µmol $m^{-2}$ $s^{-1}$.

GC/MS analysis of the fatty acid composition of *Nannochloropsis* strain LARB-AZ 0202.0 showed that the medium chain fatty acids (C14 and C16) represented ca. 72% and the long chain fatty acids (C18 through C20) represented approximately 28% of total fatty acids in the cells. The content of medium chain fatty acids in *Nannochloropsis* strain LARB-AZ 0202.0 is the highest or among the highest in *Nannochloropsis* strains reported thus far (Table 1).

TABLE 1

Comparison of Fatty Acids Profiles of *Nannochloropsis* LRB-AZ 0202.0 and other *Nannochloropsis* strains published in literature.

| Fatty Acids | LRB-AZ 0202.0 | *N.* sp Hu et al., 2003 | *N.* sp Roncarati et al., 2004 | *N. oculata* (Droop) | *N.* sp Xu et al., 2004 | *N.* sp Fang et al., 2004 | *N.* sp | *N.* sp Kobayashi et al., 2008 NLP PLP | *N.* sp Gouveia et al., 2009 | *N. occanica* Seychelles et al., 2009 | Patil et al., 2007 |
|---|---|---|---|---|---|---|---|---|---|---|---|
| C14:0 | 3.32 | 4.1-5.7 | 2.51 | 2.39 | 5.2 | 4.3 | 4.6 | 3.6 | 7.16 | 16.9 | 16.9 |
| C14:1 | 0.04 | | | 0.02 | | | | | | | |
| C15:0 | 0.36 | | 0.48 | 0.65 | | | | | | | |
| C15:1 | 0.23 | | | | | | | | | | |
| C16:0 | 41.79 | 24.4-31.8 | 14.39 | 14.53 | 25.1 | 24.6 | 20.3 | 21.3 | 23.35 | 17.2 | 17.2 |
| C16:1 | 27.54 | 25.1-27.9 | 19.49 | 15.67 | 27.1-30.8 | 30.2 | 17.5 | 14.4 | 26.87 | 18.2 | 18.2 |
| C17:1 | 0.04 | | 10.50 | 4.12 | | | | | | | |
| C18:0 | 1.56 | 0.5-1.2 | 11.28 | 1.83 | 1.1-2.1 | 1.1 | 0.6 | 0.3 | 0.45 | 1.8 | 1.8 |
| C18:1 n9c | 16.03 | 7.1-10 | 5.59 | 10.12 | 7.1-10.4 | 11.0 | 7.4 | 7.6 | 13.20 | 4.1 | 4.1 |
| C18:2 n6t | 0.01 | 2.9-4.5 | 6.77 | 3.61 | | | 5.7 | 7.6 | 1.21 | 9.7 | 9.7 |
| C18:2 n6c | 0.30 | | | | | | | | | | |
| C20:0 | 0.06 | 0.2-0.3 | 3.09 | 1.96 | | | 0.1 | 0.1 | | | |
| C18:3 n6c | 0.04 | | 1.69 | 1.87 | | | 0.2 | 0.3 | | 0.5 | 0.5 |
| C18:3 n3 | 0.02 | | 1.88 | 0.65 | | | 6.7 | 5.8 | | | |
| C20:1 | 0.01 | 0.6-1.2 | | 0.91 | | | 0.2 | 0.2 | | 0.5 | 0.5 |
| C21:0 | 0.03 | | | | | | | | | | |
| C20:2 | 0.03 | | | | | | 0.2 | 0.2 | | 0.5 | 0.5 |
| C22:0 | 0.01 | | | | | | 0.1 | 0.1 | | | |
| C20:3 n6c | 0.73 | | 0.81 | 0.53 | | | 0.1 | 0.2 | | | |
| C20:5 | 7.55 | 18-25.3 | 18.24 | 21.48 | 20.1-30.9 | 21.8 | 25.8 | 26.7 | 14.31 | 23.4 | 23.4 |

Characterization of *Nannochloropsis* Strain LARB-AZ 0202.0 Under Laboratory Conditions Effect of light intensity and nitrogen concentration on growth, total and neutral lipid contents and productivity of algal biomass and lipids of LARB-AZ 0202.0. In order to assess the potential of using LARB-AZ 0202.0 as a candidate strain for production of medium chain fatty acids, the effects of nitrogen concentration on growth and production of algal biomass and lipid under low light and high light conditions were investigated under controlled laboratory culture conditions. Four nitrogen concentrations (i.e., 0.01, 0.06, 0.12 and 0.24 g $L^{-1}$ nitrogen as nitrate) and two light levels (20 and 350 µmol $m^{-2}$ $s^{-1}$) were selected for the study. As shown in FIG. 1, LARB-AZ 0202.0 grew rapidly at the low and high light intensities for the first 3 to 5 days and then leveled off as the cultures continued. The maximum cell concentration in the cultures with the initial nitrogen concentration of 0.26 g $L^{-1}$ at 350 photons $m^{-2}$ $s^{-1}$ was about twice of that obtained in the low light cultures. As the initial nitrogen concentration decreased from 0.24 g $L^{-1}$ to 0.01 g $L^{-1}$, the growth rate decreased accordingly and the differences in growth between the cultures at low light and high light became smaller.

Figure 2:
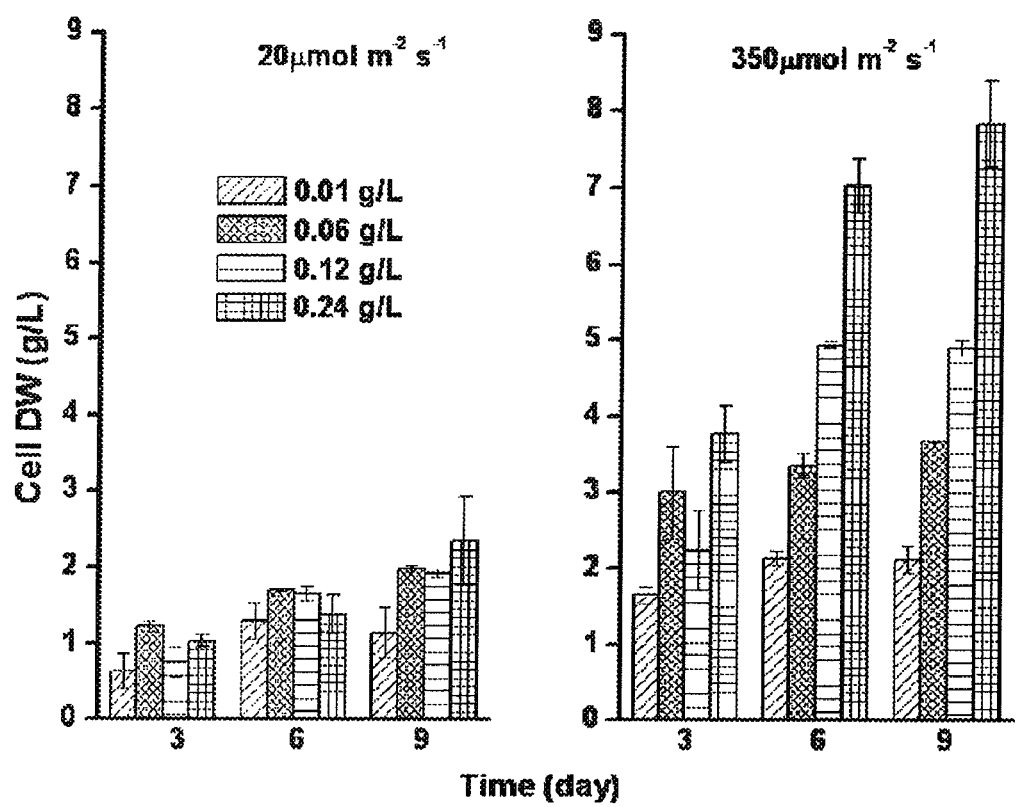
FIG. 2: Effect of initial nitrogen concentrations on cell dry weight of the cultures at 20 and 350 µmol $m^{-2}$ $s^{-1}$. Algal samples were taken on day 3, 6 and 9 of cultivation. Culture conditions were the same as in FIG. 1.

FIG. 2 shows cell dry weights of LARB-AZ 0202.0 cultures maintained at the different initial nitrogen concentrations and light intensities. The maximum final cell concentrations of 2.4 g $L^{-1}$ and 8.0 g $L^{-1}$ were obtained in the cultures with the highest initial nitrogen concentration of 0.24 g L–1 at low and high light intensities, respectively. Compared to the low light cultures, the final cell concentration in the high light cultures was affected to a larger extent by the initial nitrogen concentration; i.e., the higher the initial nitrogen concentration, the high the final cell density of the culture.

Figure 3:
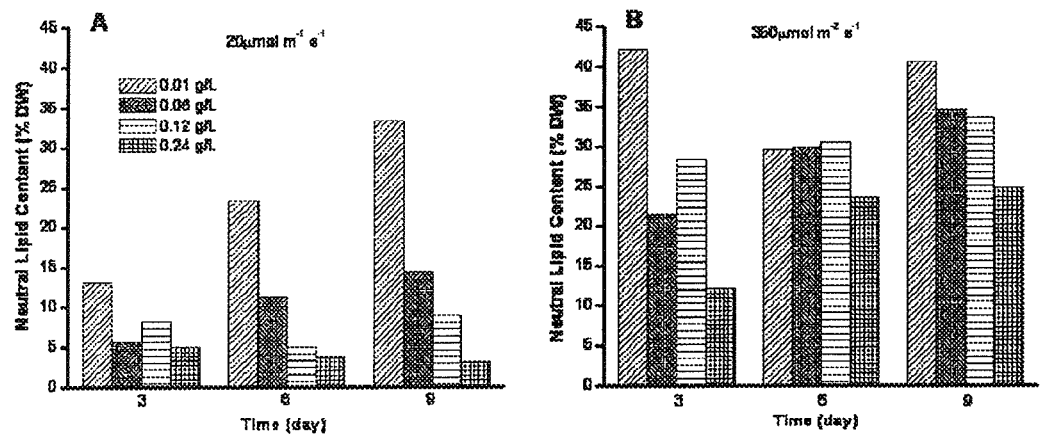
FIG. 3: Effect of different initial nitrogen concentrations and light intensities on cellular neutral lipid content of LARB-AZ 0202.0. Culture conditions were the same as in FIG. 1.

Initial nitrogen concentration and light intensity not only affected growth but neutral lipid content of LARB-AZ 0202.0. A reverse correlation was observed between the initial nitrogen concentration and neutral lipid content in the cells in the cultures. Under low light of 20 μmol photons $m^{-2}$ $s^{-1}$, the lowest neutral lipid content of >5% of cell dry weight (DW) occurred in the cultures containing the highest initial concentration of nitrogen, whereas the highest neutral lipid content of 36% of DW was observed in the cultured with the lowest initial nitrogen concentration (FIG. 3A). The trend was also true for the cultures exposed to the high light, although the differences in the maximum cellular neutral lipid content were less drastic between the low and high nitrogen cultures (FIG. 3B). Accordingly, the maximum neutral lipid content of the lowest nitrogen culture was ca. 22% of DW, whereas that of the highest nitrogen cultures was about 42% of DW (FIG. 3B).

Figure 4:
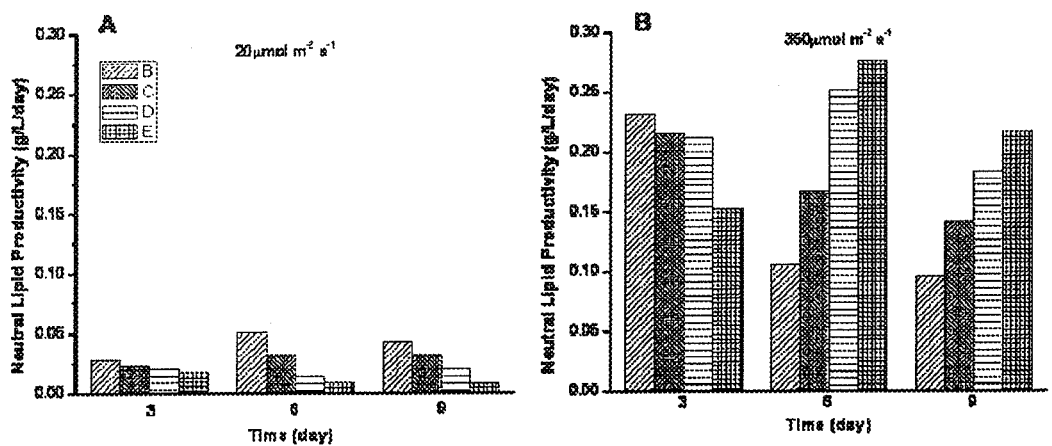
FIG. 4: Productivity of neutral lipid in LARB-AZ 0202.0 cultures grown at low and high light intensities in the presence of the different initial nitrogen concentrations. The experimental conditions were the same as described in FIG. 1.

Neutral lipid productivity was calculated from growth and neutral lipid content data obtained from the experiments described above and the results are shown in FIG. 4. The maximum neutral lipid productivity of 0.06 g $L^{-1}$ $d^{-1}$ was obtained in the low light cultures with the lowest initial nitrogen concentration of 0.01 g $L^{-1}$ (FIG. 4A), whereas the maximum neutral lipid yield of 0.28 g $L^{-1}$ $d^{-1}$ was obtained from the high light cultures containing the highest initial nitrogen concentration (FIG. 4B).

Productivity of algal biomass and total lipid (sum of neutral lipid polar lipid) in cultures of LARB-AZ 0202.0 was compared with that reported with other *Nannochloropsis* strains in the literature. As shown in Table 2, *Nannochloropsis* strain LARB-AZ 0202.0 has the ability to produce the greatest amounts of biomass and total lipid among the *Nannochloropsis* strains reported thus far under laboratory culture conditions.

TABLE 2

Comparison of lipid and biomass productivities of *Nannochloropsis* strain LRB-0202.0 with other *Nannochloropsis* strains reported in the literature.

| Strain | Culture mode | Illumination | Culture device | Cell density/mass | Lipid content | Biomass productivity | Lipid productivity | Reference |
|---|---|---|---|---|---|---|---|---|
| *N. oculata* | Indoor Batch | Continuous 70 μmol/m²/s | 2.0 L flasks | N/A | 14.7% DW | N/A | 0.02 g/L/day | Converti et al., 2009 |
| *N. gaditana* | Semi-continuous | Light/Dark 12:12(h) | Glass tubes D30 mm | 2.23 × 10⁸/ml | 1.57 pg · cell⁻¹ | N/A | N/A | Ferreira et al., 2009 |
| *N. oculta* | Batch | 162 μmol/m²/s Continuous 1000 Lx | 1.1 L columns D69 mm | 1.4 g/L | 25.1% DW | N/A | N/A | Hsueh et al., 2009 |
| *N.* sp F&M-M26 | Batch | Continuous 100 μmol/m²/s | 250 ml flasks | N/A | 29.6% DW | 0.21 g/L/day | 0.061 g/L/day | Rodolfi et al., 2009 |
| *N.* sp F&M-M27 | Batch | Continuous 100 μmol/m²/s | 250 ml flasks | N/A | 24.4% DW | 0.20 g/L/day | 0.048 g/L/day | Rodolfi et al., 2009 |
| *N.* sp F&M-M24 | Batch | Continuous 100 μmol/m²/s | 250 ml flasks | N/A | 30.9% DW | 0.18 g/L/day | 0.055 g/L/day | Rodolfi et al., 2009 |
| *N.* sp F&M-M29 | Batch | Continuous 100 μmol/m²/s | 250 ml flasks | N/A | 21.6% DW | 0.17 g/L/day | 0.038 g/L/day | Rodolfi et al., 2009 |
| *N.* sp F&M-M24 | Semi-continuous | Continuous 200 μmol/m²/s | 0.6 L tubes D45 mm | N/A | 63% DW | 0.80 g/L/day | 0.055 g/L/day | Rodolfi et al., 2009 |
| *N. oculata* | Semi-continuous | Continuous 300 μmol/m²/s | Glass cylinders D70 mm | 1.28 g/L | 29.7% DW | 0.48 g/L/day | 0.142 g/L/day | Chiu et al., 2009 |
| *N. oculata* | Semi-continuous | Continuous 300 μmol/m²/s | Glass cylinders D70 mm | N/A | 30.7% DW | 0.497 g/L/day | 0.151 g/L/day | Chiu et al., 2009 |
| *N. oculata* | Semi-continuous | Continuous 300 μmol/m²/s | Glass cylinders D70 mm | N/A | 41.2% DW | 0.296 g/L/day | 0.121 g/L/day | Chiu et al., 2009 |
| *N.* sp (PP983) | Batch | Continuous 50 μmol/m²/s | 250 ml flasks | 0.22 g/L | 62% DW | N/A | N/A | Hu et al., 2006 |
| *N.* sp | Batch | Continuous 73 μmol/m²/s | 250 ml flasks | 0.51 g/L | 42.7% DW | N/A | N/A | Fang et al., 2004 |
| *N.* sp | Semi-continuous | Light/Dark 12:12(h) 0-480 μmol/m²/s | 120 ml Pyrex D30 mm | 1.15 × 10⁸/ml | 33.25% DW | 0.376 g/L/day | N/A | Fabregas et al., 2004 |
| *N.* sp | Batch | Continuous 50 μmol/m²/s | 10 L Scott glass bottles | 0.633 g/L | 9% DW | N/A | N/A | Hu et al., 2003 |
| *N.* sp | Batch | Light/Dark 12:12(h) 100 μmol/m²/s | 100 L Polyethylene bags | 2.43 × 10⁷/ml | 1.1 pg · cell⁻¹ | N/A | N/A | Dunstan et al., 1993 |
| *N. oculata* | Batch | Continuous 65 μmol/m²/s | 2 L Scott glass bottles | 9.5 pg · cell⁻¹ | 58% DW | N/A | N/A | Hodgson et al., 1991 |
| *N. salina* | Batch | Continuous 50 μmol/m²/s | 10 L flasks | 3 × 10⁷/ml | 50% DW | N/A | N/A | Emdadi et al., 1989 |
| *N.* sp QII | Batch | Continuous 62 μmol/m²/s | Fernbach flasks/Roux bottles | 2 g/L | 55% AFDW | 0.33 g/L/day | 0.18 g/L/day | Suen et al., 1987 |

TABLE 2-continued

Comparison of lipid and biomass productivities of Nannochloropsis strain
LRB-0202.0 with other Nannochloropsis strains reported in the literature.

| Strain | Culture mode | Illumination | Culture device | Cell density/mass | Lipid content | Biomass productivity | Lipid productivity | Reference |
|---|---|---|---|---|---|---|---|---|
| N. sp. LRB-AZ 0202.0 | Batch | Continuous 350 µmol/m²/s | 600 ml glass tubes D38 mm | 11.2 g/L | 58% DW | 0.88 g/L/day | 0.52 g/L/day | Shan et al., 2009 |

Figure 5:
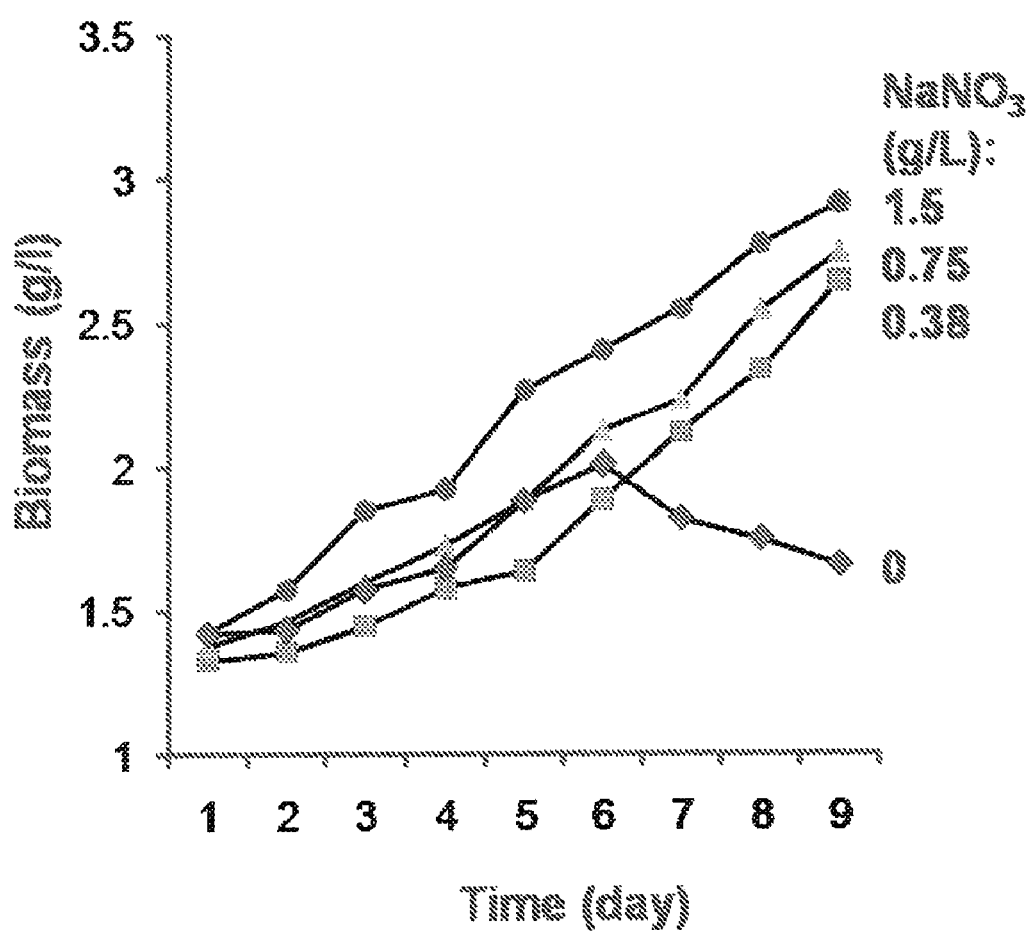
FIG. 5: Effect of initial nitrate concentrations on growth of LARB-AZ 0202.0 in the photobioreactor (PBR) at ASU Algae Test Bed Facility, ASU Polytechnic campus, Mesa, Ariz. The experiment was conducted in June, 2009. PBR measured wide×high×depth=4'×4'×1.5". Each PBR unit contained ca. 50 liters of culture.
Figure 6:
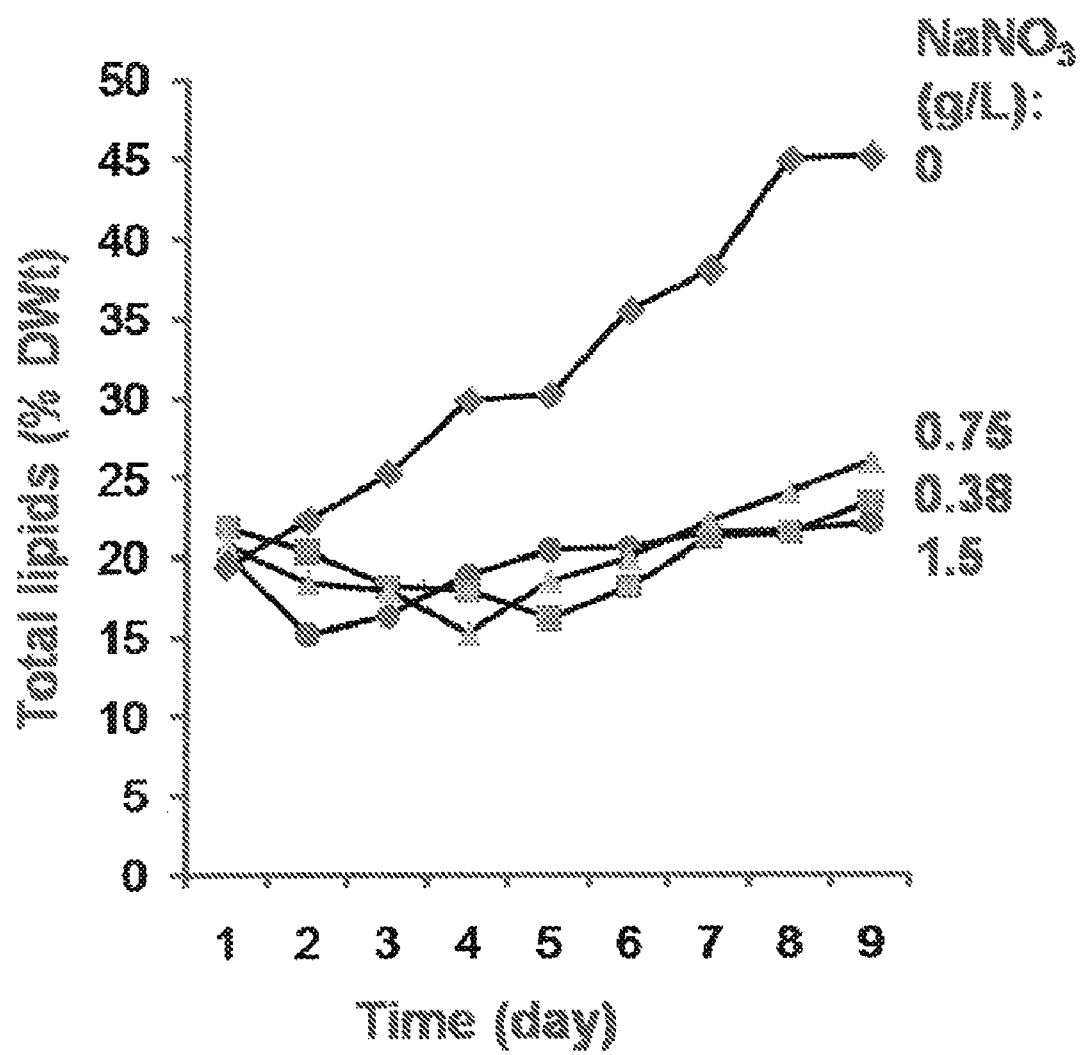
FIG. 6: Effect of initial nitrate concentrations on the cellular lipid content of LARB-AZ 0202.0 grown in PBR outdoors. The culture conditions were the same as in FIG. 5.

Optimization of *Nannochloropsis* Strain LARB-AZ 0202.0 Cultures Under Outdoor Environmental Conditions Effect of initial nitrogen concentrations on biomass and lipid production of LARB-AZ 0202.0 grown in a flat panel photobioreactor outdoors. When inoculated from a seed culture into the flat panel photobioreactor (PBR) that contained F/2 culture media varying in initial nitrogen concentrations ranging from 0.38 to 1.5 g $L^{-1}$ NaNO3, LARB-AZ 0202.0 cells exhibited the different growth kinetics, as shown in FIG. 5. The cultures containing 1.5 g $L^{-1}$ NaNO3 exhibited the highest growth, reaching ca. 3 g $L^{-1}$ of cell dry weight after 9 days of cultivation. The lower concentrations of nitrate in the cultures resulted in somewhat reduced growth during the same period of cultivation. The cultures with the lowest nitrate concentration exhibited rapid growth for the first 6 days and then declined gradually as the culture proceeded.

The cells that were used for the experiment contained about 20% of total lipid on a per cell dry weight basis. The total lipid decreased somewhat in the cultures containing 0.38, 0.75 and 1.5 g $L^{-1}$ of nitrate during the first 2-4 days and then recovered or slightly increased. By the end of cultivation, the total lipid in the cells was below 25% of cell dry weight. In contrast, the cultures in the absence of external nitrate supply experienced rapid increase in cellular total lipid from ca. 20% to 45% of total lipids during the same period of time. It was concluded that deprivation of nitrogen in the growth medium is a prerequisite for triggering lipid synthesis and accumulation in algal cells.

Figure 7:
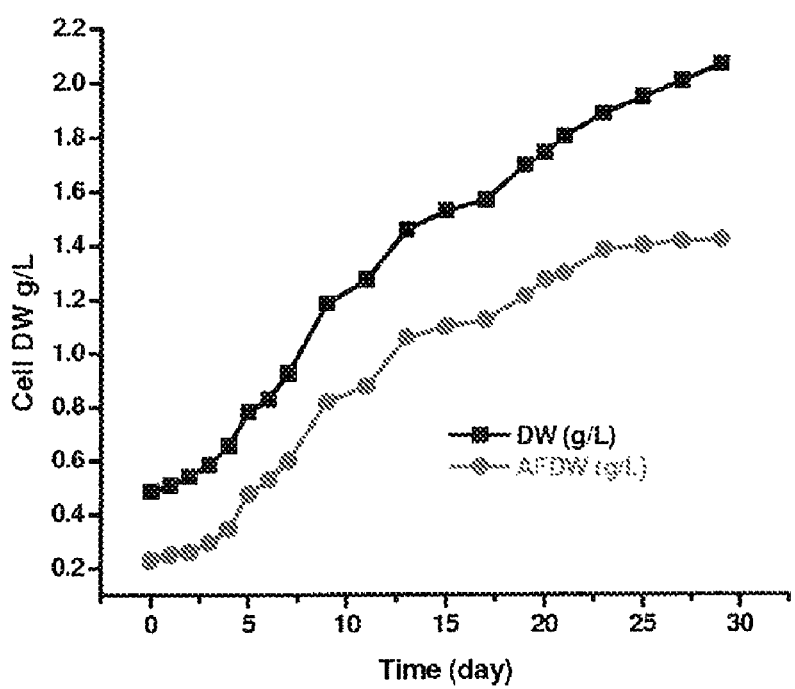
FIG. 7: A) Increase in cell dry weight (DW) and ash-free dry weight (AFDW) (FIG. 7A) with concomitant decrease in nitrogen concentration (FIG. 7B) in the raceway cultivation of LARB-AZ 0202.0 outdoors.
Figure 7:
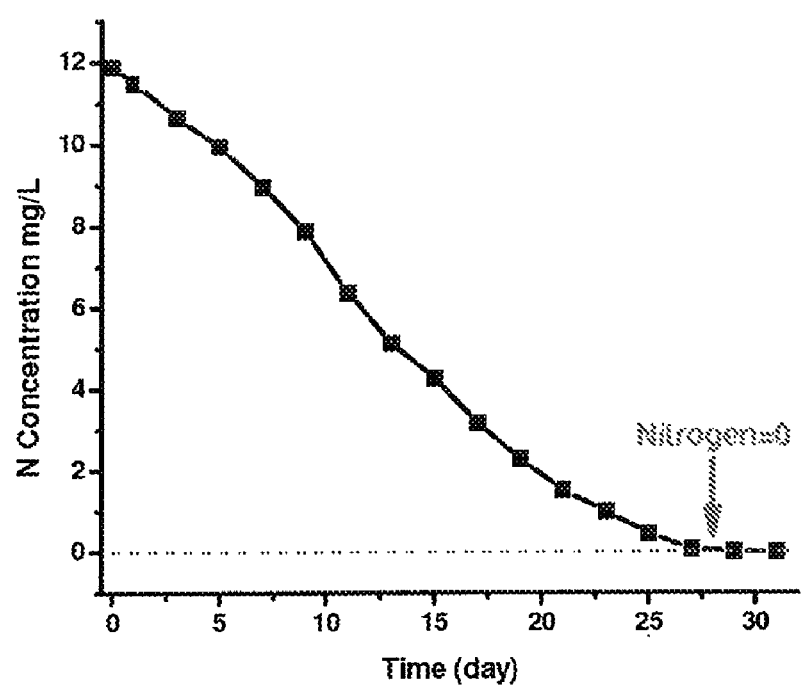

Effect of initial cell concentrations on growth, lipid content and productivity of LARB-AZ 0202.0 in the flat panel photobioreactor outdoors. The effects of initial cell concentrations on growth, lipid content and productivity of LARB-AZ 0202.0 in the PBR were investigated in October, 2009. The seed culture was maintained in an open raceway pond adjacent to the PBR for 4 weeks. The cell concentration in the pond prior to the experiment was 2.21 g $L^{-1}$ (FIG. 7A) and the nitrate was completely depleted from the culture medium (FIG. 7B).

For the initial cell density experiment, algal suspension from the seed culture was diluted to various extents, as shown in Table 3.

TABLE 3

Treatment ID, dilution factor, initial cell counts and initial cell dry weight of seed culture for the cell density experiment.

| Treatment | Dilution factor (times, x) | Initial cell counts (×10⁸ ml⁻¹) | Initial cell dry weight (g $L^{-1}$) |
|---|---|---|---|
| A | 8× | 0.4 | 0.42 |
| B | 4× | 0.8 | 0.64 |
| C | 2× | 1.2 | 1.14 |
| D | 1.5× | 1.4 | 1.56 |
| E | 0 | 1.6 | 2.21 |

Figure 8A:
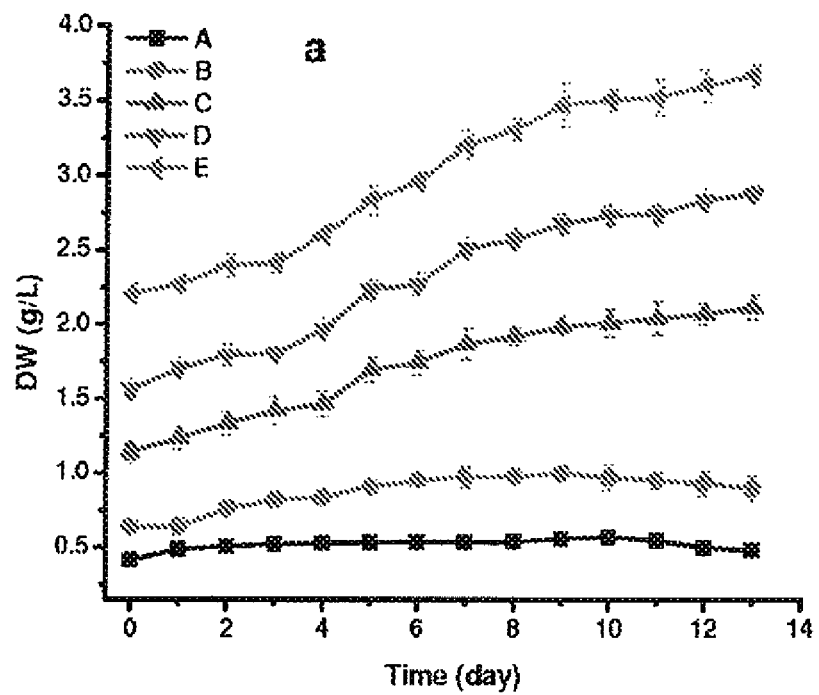
FIG. 8: Effect of initial cell concentration on growth of LARB-AZ 0202.0 in the PBR outdoors.
Figure 8B:
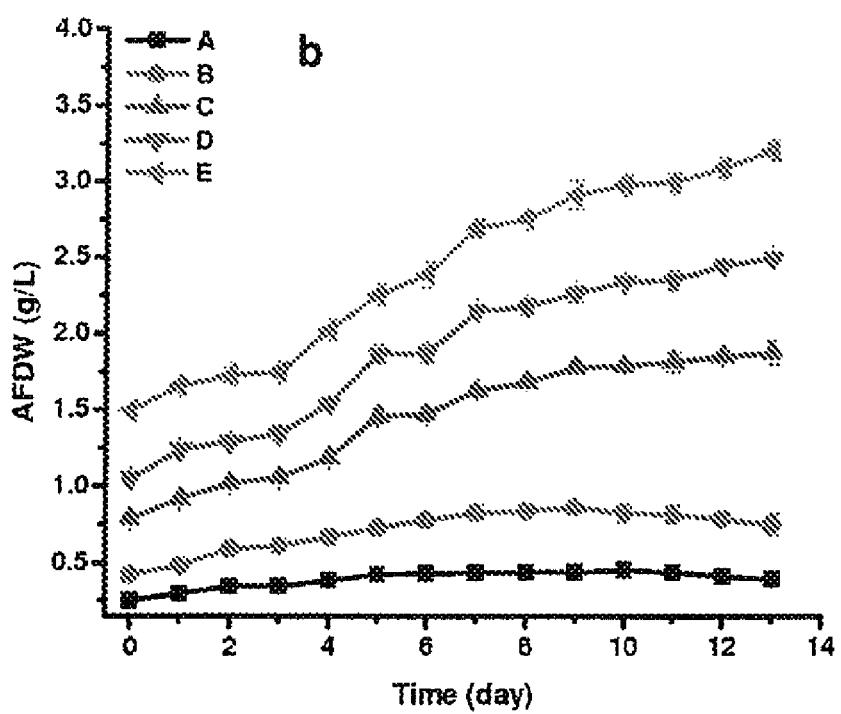

FIG. 8 shows the growth kinetics of LARB-AZ 0202.0 cultures as a function of initial cell concentrations on a dry weight (a) and ash-free dry weight (b) basis. When the initial cell concentration was equal or below 0.64 g $L^{-1}$, growth was slower than that with the initial cell concentration of equal or greater than 1.14 g $L^{-1}$.

Figure 9A:
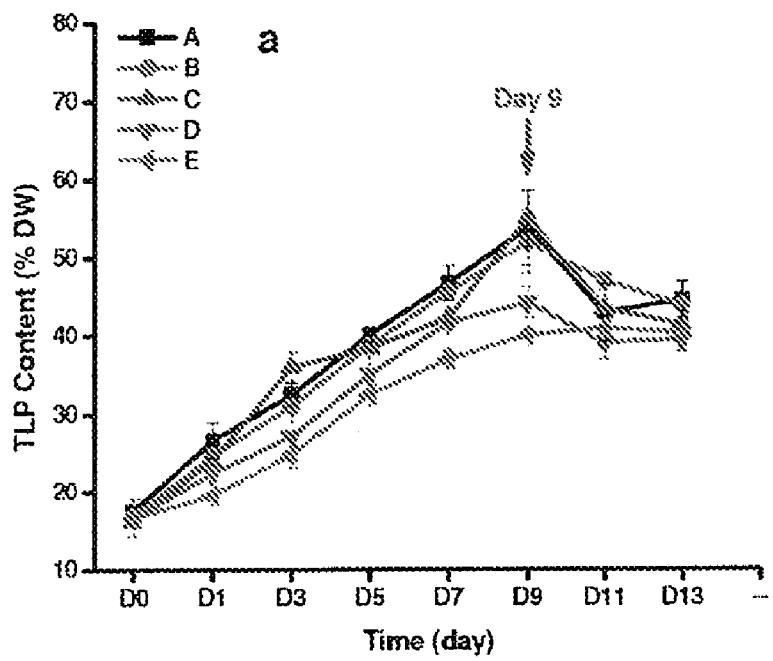
FIG. 9: Effect of initial cell concentration on total lipid content of LARB-AZ 0202.0 in the PBR outdoors.
Figure 9B:
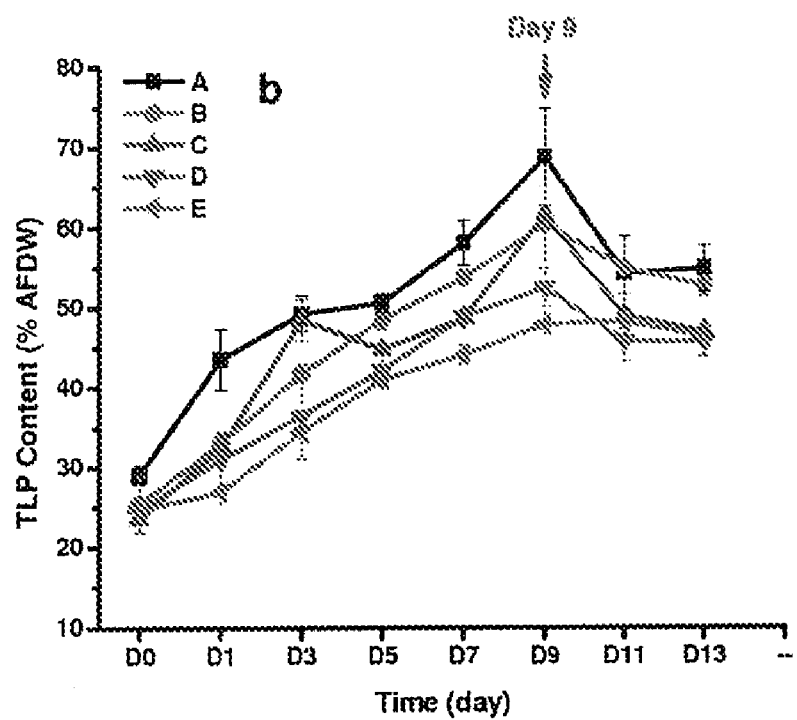
Figure 10A:
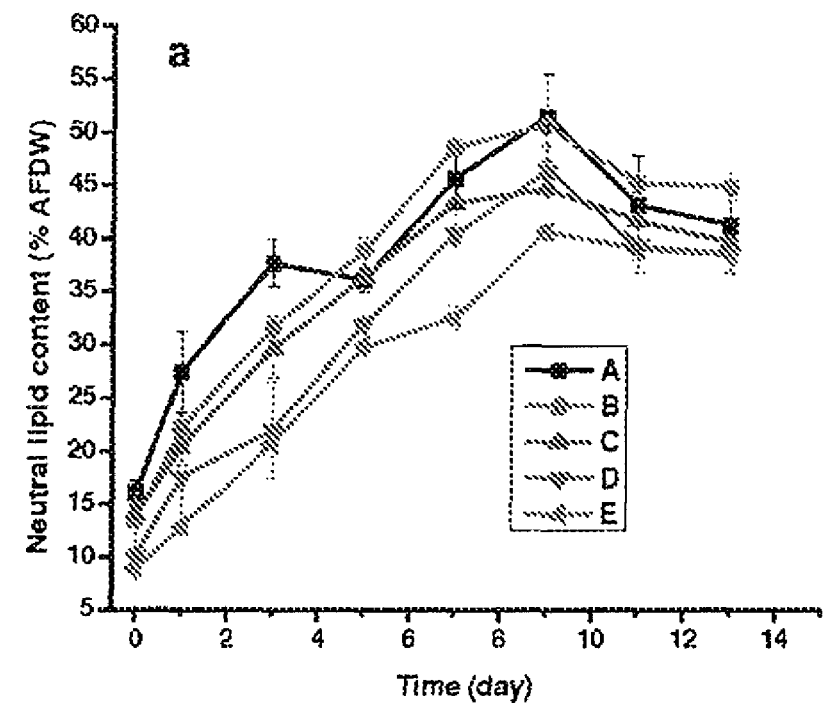
FIG. 10: Effect of initial cell concentration on neutral lipid content of LARB-AZ 0202.0 in the PBR outdoors.
Figure 10B:
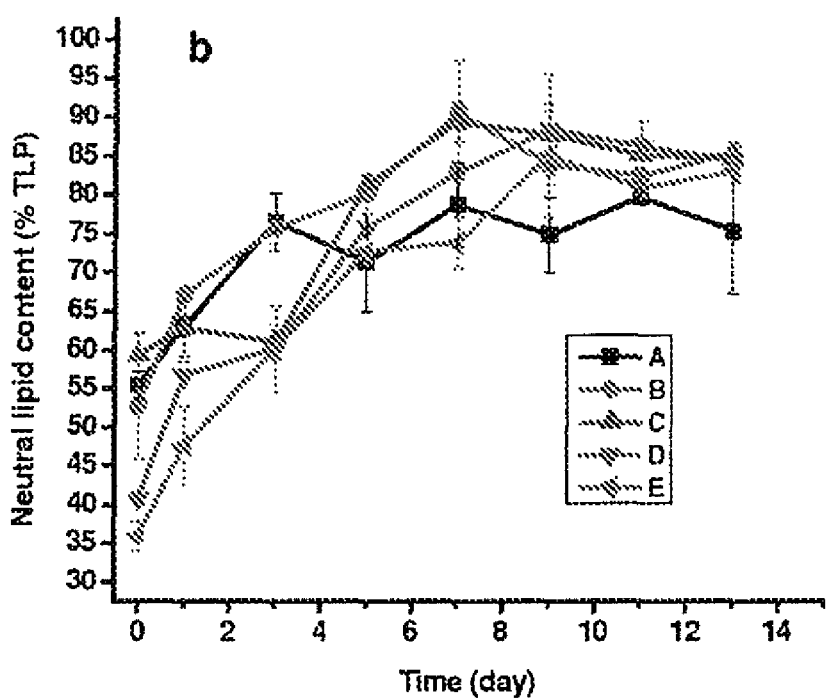
Figure 11A:
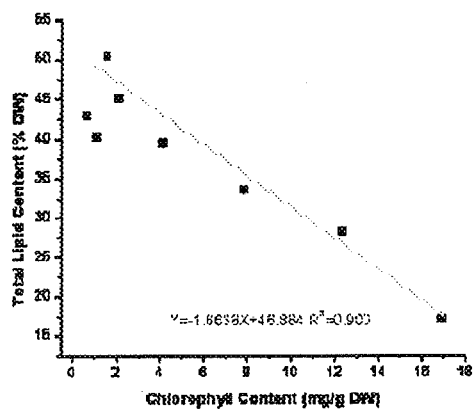
FIG. 11: Correlation between the lipid content (both total lipid/neutral lipid) and pigment content (both chlorophyll and carotenoids) in *Nannochloropsis* strain LARB-AZ 0202.0 grown in a thin panel PBR outdoors. Initial cell density of the cultures was OD 0.6 at 750 nm.
Figure 11B:
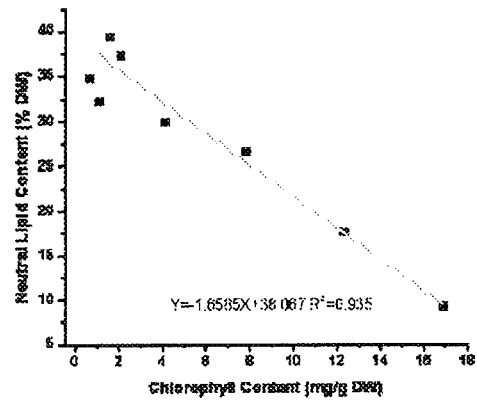
Figure 11C:
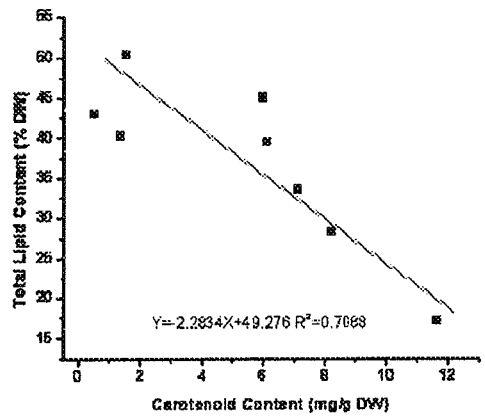
Figure 11D:
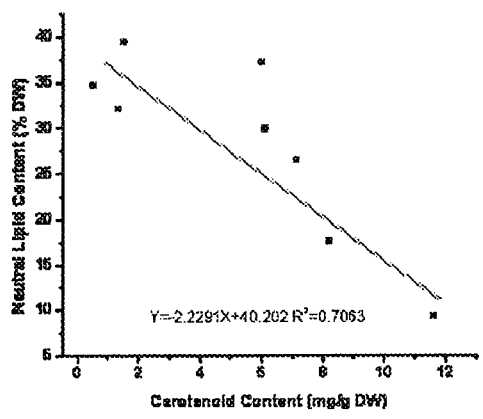

Initial cell concentration in the PBR also affected cellular lipid content. The highest total lipid content of nearly 70% of DW was observed in the cultures with the lowest initial cell concentration after 8 to 9 days of cultivation (FIG. 9a, b). The highest initial cell concentration resulted in the lowest maximum lipid content of 45% of DW in the cells. The neutral lipid content essentially followed the same trend (FIG. 10).

Figures 12A, 12B, 12C, 12D:
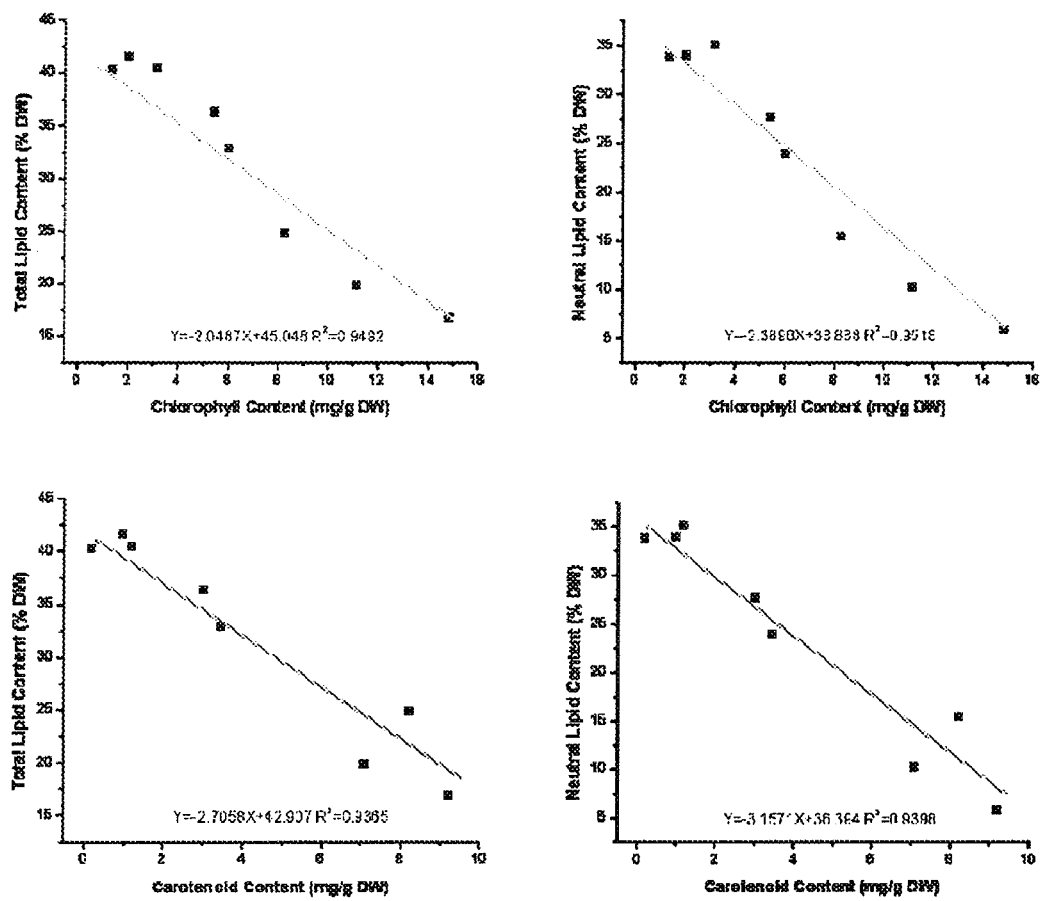
FIG. 12: Correlation between the lipid content (both total lipid/neutral lipid) and pigment content (both chlorophyll and carotenoids) in *Nannochloropsis* strain LARB-AZ 0202.0 grown in a thin panel PBR outdoors. Initial cell density of the cultures was OD 1.6 at 750 nm.

Correlation between the content of lipids and pigments in *Nannochloropsis* strain LARB-AZ 0202.0 grown in flat plate PBR outdoors. A reverse relationship between the carotenoid content and lipid (including total lipid and neutral lipid) was observed in *Nannochloropsis* strain LARB-AZ 0202.0 grown in flat plate PBR outdoors. As shown in FIG. 11, the higher the lipid content (both neutral lipid and total lipid) the lower the pigment content (both chlorophyll and carotenoid). A higher initial cell density showed the same trend, though the slope of the correlation fit was somewhat different (FIG. 12).

Quantitative measurement of lipid, particularly neutral lipid by conventional gravimetric methods is time- and labor-intensive. In contrast, spectrophotometric measurement of the chlorophyll and carotenoid content is simple and straight forward. The correlation between the lipid and pigment contents in the cell that are established in this invention can be applied to commercial large-scale cultivation of algae for lipid/oil production. The cellular content of total lipid and neutral lipid can be calculated by measuring the chlorophyll and/or carotenoid content in the cells.

Strain improvement by chemical mutagenesis. In order to further improve the performance and/or the lipid content of *Nannochloropsis* strain LARB-AZ 0202.0, a chemical mutagenesis approach was applied to the parental strain, followed by a screening and selection process to obtain superior strains to the parental strain. Two mutants, i.e., LARB-AZ 0202.2 and LARB-AZ 0202.3 have been generated and partially characterized. The mutants and the parental strain were cultured in a glass column PBR mixed with compressed air containing 1% CO2. Cultures were exposed to continuous illumination of light intensity ranging from 140 to 300 photons $m^{-2} s^{-1}$. Overall biomass productivity of all three strains were higher under high light (HL, 300 µmol photons $m^{-2} s^{-1}$) with LARB-AZ 0202.3 achieving the highest volumetric productivity (0.9 g $L^{-1} d^{-1}$) and parent wild type the lowest (0.72 g $L^{-1} d^{-1}$). Biomass productivity of all three strains substantially decreased in response to low light (140 µmol photons $m^{-2} s^{-1}$) growth conditions. However, LARB-AZ 0202.3 mutant showed the highest biomass productivity (0.74 g $L^{-1} d^{-1}$) under low light conditions as well. LARB-AZ 0202.3 mutant possessed high photosynthetic productivity as measured by chlorophyll a (Chl a) content under HL conditions throughout the growth period. Cellular content of chlorophyll per dry weight declined gradually in all three tested strains over time. Volumetric productivity of biomass was closely associated with the volumetric productivity of chlorophyll. Total lipid and neutral lipid productivity of LARB-AZ 0202.2 mutant grown in nitrogen deprived media for 7 days were 222 and 174 mg $L^{-1}$ $d^{-1}$, respectively, while those of wild type parent was 202 and 151 mg $L^{-1}$ $d^{-1}$, respectively. A comparison of the fatty acid profile of LARB-AZ 0202.2 mutant with its parent wild type confirmed a significant increase of C14:0 and C16:0 in the mutant. Total medium chain fatty acids that contribute directly to MCFA-rich oil production had an overall increase of 12.2 percent over that of wild type parent.

Outdoor cultivation of LARB-AZ 0202.0-derived mutants LARB-AZ 0202.2 and LARB-AZ 0202.3 Cultivation of the *Nannochloropsis* mutants LARB-AZ 0202.2 and LARB-AZ 0202.3 was also conducted in a flat panel photobioreactor outdoors. Culture conditions: growth medium-f/2 with 0.25 amount of Sodium Nitrate (0.18 g/L); Replicates: three; constant supply of CO2 1%; Temperature was controlled during the day time with cooling system and never exceeded 28° C.; pH ranged between 7.6 to 9.2; Maximum light intensity ranged between 800-15600 μmol photons $m^{-2}$ $s^{-1}$.

Figure 14A:
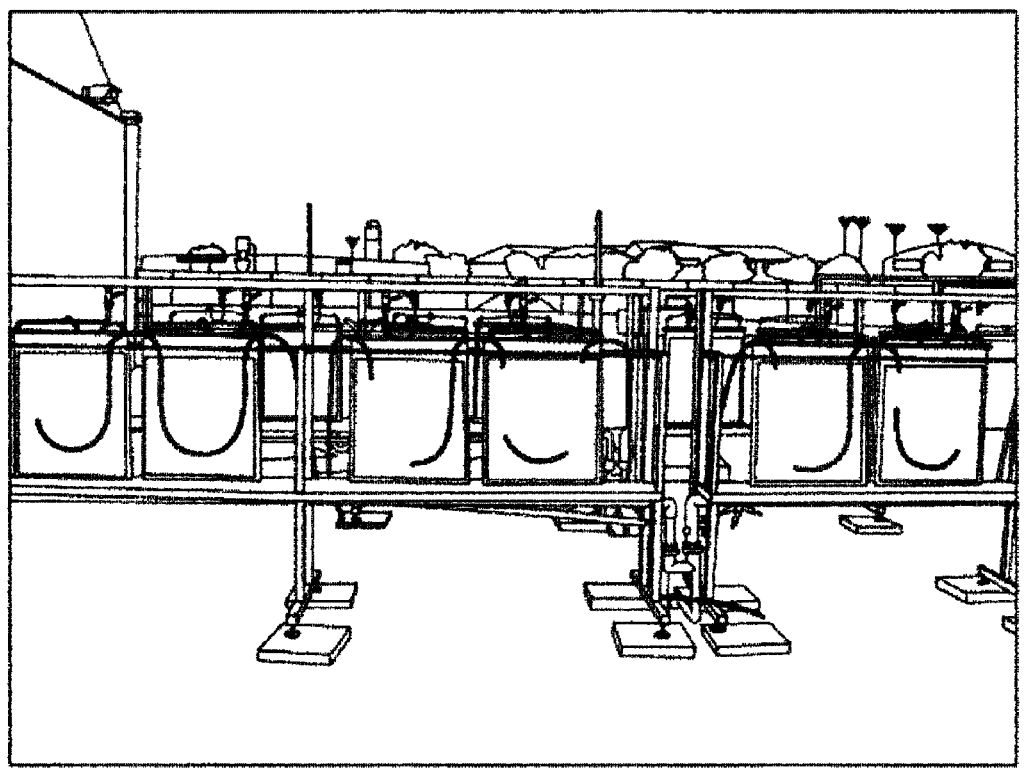
FIG. 14A: $4^{th}$ day observation of mutant LARB-AZ 0202.2 (dark color) and wild type *Nannochloropsis* LARB-AZ 0202.0 (light color) grown in the flat panel photobioreactors outdoors.

As shown in FIGS. 14A, B and 15A, B, the two mutants LARB-AZ 0202.2 and LARB-AZ 0202.3 grew more rapidly than the wild type LARB-AZ 0202.0 under identical culture conditions.

Materials and methods. Preparation of culture media for mutation experiment: The parent wild type *Nannochloropsis* strain LARB-AZ 0202.0 was maintained in a modified Guillard f2 medium (Guillard and Ryther, 1962) containing 0.75 g $NaNO_3$ $L^{-1}$ $NaNO_3$ and 0.03 g $L^{-1}$ $NaH_2PO_4$. Cultures were maintained at 21±1 C.° and a light intensity of 50-60 photons $m^{-2}$ $s^{-1}$. Cultures at early log-phase ($3\times10^7$ cells $ml^{-1}$) were subjected to chemical mutagenesis.

Experimental design: The mutation program used ethyl methane sulphonate (EMS) solution as mutagenic agent. The first step in the mutation program was to determine the appropriate concentration of EMS and time of treatment for the parent culture, and to determine the survival rate under the EMS treatment.

Survival count: Preliminary analysis of survival data with EMS concentrations ranging from 25 to 100 μL/mL showed that EMS treatment of 50 μL/mL could produce a wide range (0.3 to 87 percent) of survival rates depending on the duration of treatment.

To determine the effect of EMS treatment duration on cell survival, exponentially grown parental cells (approximately $3.0\times10^7$ cells/ml) were transferred to a test tube containing a potassium buffer, pH 7. The cells were treated with 50 μL/mL EMS (approximately 460 mmol) in a screw-cap glass tube. After incubation, the cells were treated for the different time intervals (20 to 180 min) with 7% sodium thiosulphate. Individually treated cell cultures were thoroughly washed twice with distilled water and incubated in the dark overnight prior to plating. Aliquots of the mutagenized cells were spread onto enriched f/2 medium solidified with 1% agar. Colonies on the plates were counted after 6 weeks from the time of plating. Fast growing colonies were individually inoculated into the enriched f/2 liquid medium in test tubes and grown until early log-phase. Rapid growing mutant strains were cultured for several generations and then transferred to tubular columns and grown for further screening.

Microscopic examination of culture purity and cell measurements: 2.0 ml sample was collected daily, from which an aliquot was checked under the microscope (100×). Cell count was determined using a Neubauer Haemocytometer.

Dry weight measurement: Algal dry biomass was determined daily by filtering 10 ml of the culture sample through Glass Microfiber Filters, GF/C (Whatman) The filtered sample was then washed with 10 ml of pH 4.0 double distilled water followed by 10 ml of 5% ammonium bicarbonate solution to remove adhering inorganic salts, and dried at 100 C for 24 hrs. The dried sample was immediately transferred to desiccators over silica gel for dehydration for at least 2 hrs before weighing.

Maintenance of pH: The pH of the culture was checked twice daily-morning and afternoon. The pH was maintained between 7.8 and 8.2 by adjusting the rate of CO2 flow into the air stream.

Lipid extraction and fatty acid analysis: Freeze-dried algal mass was extracted with methanol containing 10% DMSO according to Bigogno et al. (2002) but with slight modification. The biomass with added solvent was heated at 45° C. and stirred for 45 minutes after which the mixture was centrifuged at 3000 rpm for 10 min. The supernatant was removed and the pellet was re-extracted with a mixture of diethyl ether and hexane (1:1 v/v). Equal volumes of water to the solvent mixture and supernatants were added to form a ratio of 1:1:1:1 (v/v/v/v). The mixture was centrifuged again and the upper phase was collected. The water phase was re-extracted and the organic phases that contain total lipid were combined and evaporated to dryness under nitrogen protection. Total lipid with little solvent provided to dissolve was transferred to a pre-weighed Eppendorf tube, and evaporated to dryness under nitrogen protection. Thereafter, the total lipids were measured gravimetrically after freeze drying for 24 h. Neutral lipids were quantified by the method previously described by Bigogno et al. (2002). Freeze-dried total lipids were weighed and quantified by GC-MS after derivatization to fatty acid methyl esters. Fatty acids were identified by comparison with retention times of known standards. Quantitative analysis was based on known amount of heptadecanoic acid (C17:0) as the internal standard and added to the sample before injection (Chen et al., 2008; Li et al., 2010).

Figure 13A:
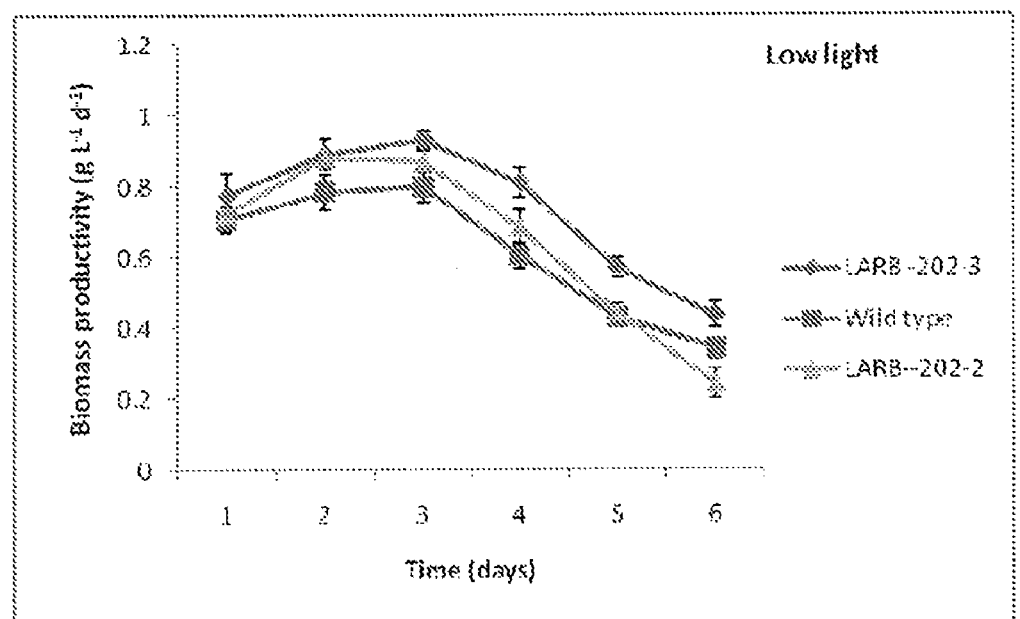
FIG. 13: Volumetric biomass productivity curves for *Nannochloropsis* wild type (LARB-AZ 0202.0; deposited with ATCC under deposit number PTA-11048 on Jun. 15, 2010), and mutants (LARB-AZ 0202.2 deposited with ATCC under deposit number PTA-11049 on Jun. 15, 2010 and LARB-AZ 0202.3 deposited with ATCC under deposit number PTA-11050 on Jun. 15, 2010. Biomass productivity is plotted as a function of time during growth. Wild type and mutant strains were cultured at 140 (LL) and 300 (HL) µmmol photons $m^{-2}$ $s^{-1}$.
Figure 13B:
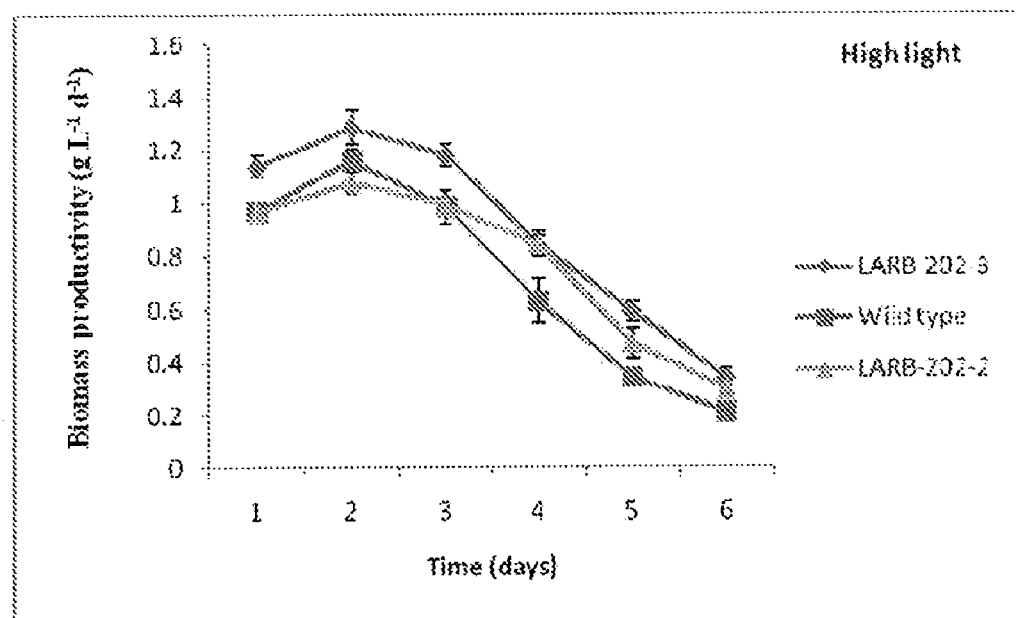
Figure 14B:
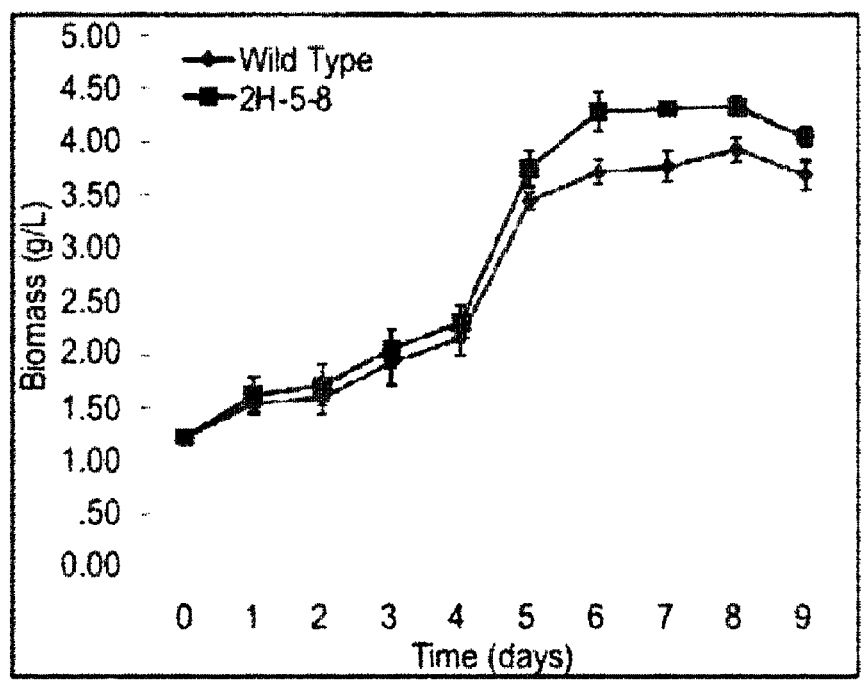
FIG. 14B: Growth kinetics of the wild type LARB-AZ 0202.0 and the mutant 211-5-8 (LARB-AZ 0202.2) in flat panel photobioreactor outdoors.
Figure 15A:
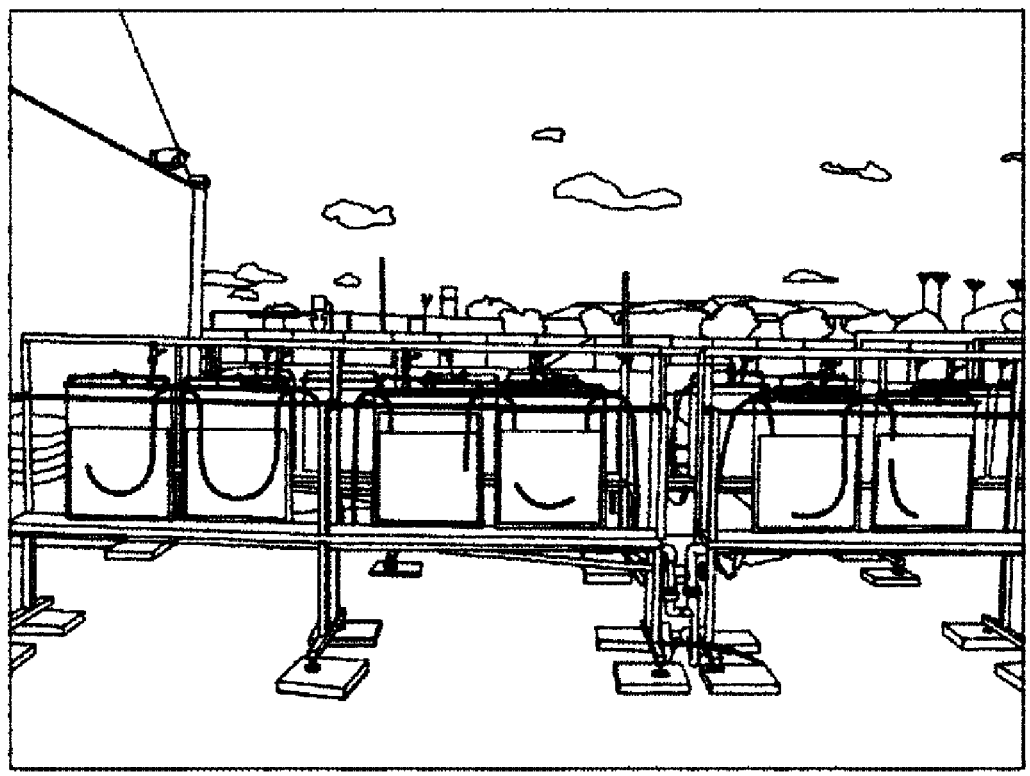
FIG. 15A: $12^{th}$ day observation of mutant LARB-AZ 0202.3 (dark color) and wild type *Nannochloropsis* LARB-AZ 0202.0 (light color).
Figure 15B:
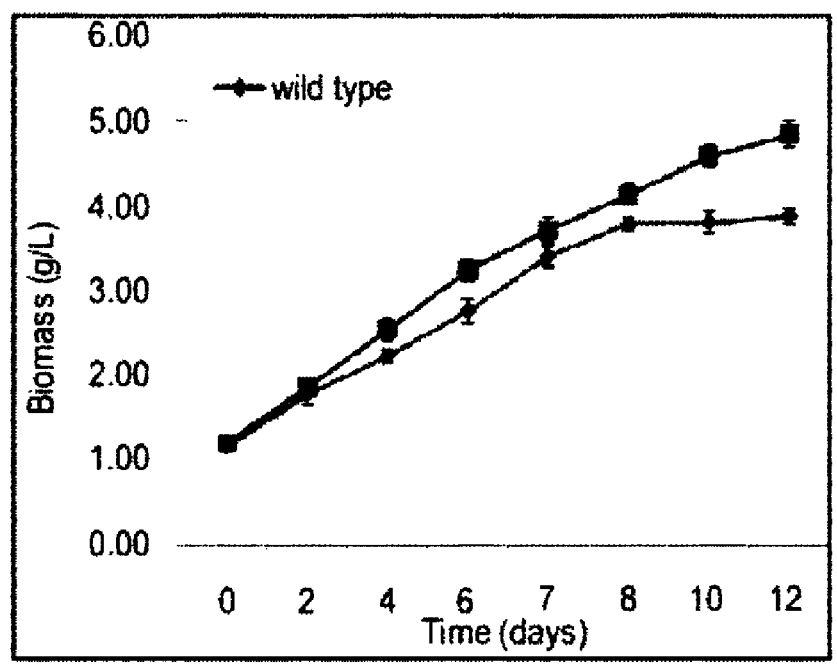
FIG. 15B. Growth kinetics of the wild type LARB-AZ 0202.0 and the mutant 2H-4-3 (LARB-AZ 0202.3) in flat panel photobioreactor outdoors.
Figure 16:
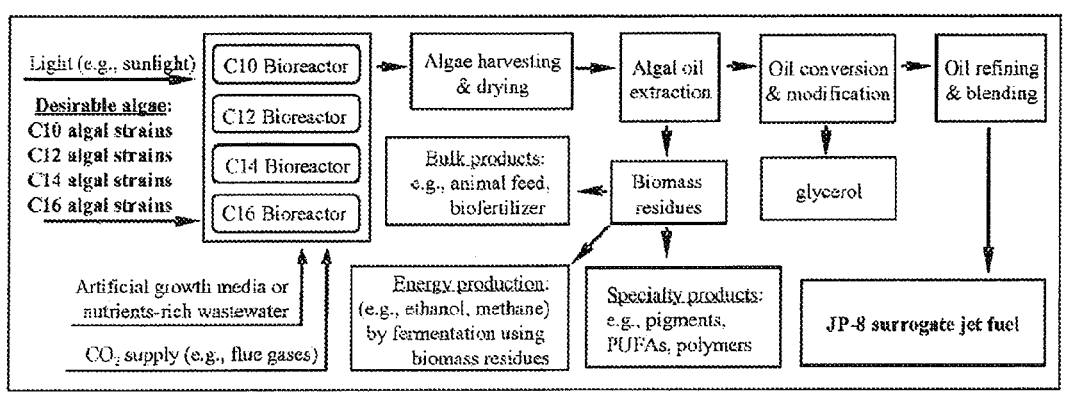
FIG. 16: Algal-based jet fuel production.

Chlorophyll a determination: Chlorophyll a was determined by a modified methanol extraction method (Azov, 1982). For high algal biomass concentrations. 1 ml of culture was centrifuged and separated in a screw-cap centrifuge tube and 4 ml methanol was added. The tubes were agitated and placed in a Buchi heating bath B-491 at 60° C. for 15 min. The samples were then cooled in the dark for 30 min and re-centrifuged. The supernatant was transferred into a 10 ml volumetric test tube and brought to a final volume of 10 ml by adding methanol. Optical density was measured against a methanol blank at 665 and 750 nm with a Spectramax 340 PC (Molecular Device) Spectrophotometer. The chlorophyll a concentration was determined by using the coefficient given by Talling (1969) in the following equation: Chlorophyll a (mg per liter)=13.9 (O.D. 665-O.D. 750).U/V In which O.D.=optical density, U=the final methanol volume, and V=the sample volume Results The mutants LARB-AZ 0202.2 and LARB-AZ 0202.3 exhibited significantly higher daily biomass productivities than the wild type strain LARB-AZ 0202.0 (FIGS. 13B and 14B).

DNA Markers for Identification of *Nannochloropsis* sp. LARB-AZ 0202.0 and the Mutants LARB-AZ 0202.2 and LARB-AZ 0202.3

For each strain, 10 ml of cultures were harvested by centrifugation at 4,000 g for 10 min. Cells were resuspended in 100 μL of buffer A that contains (1.4M NaCl, 20 mM EDTA, 100 mM Tris.HCl pH=8.0) and then mixed with another 300

µL of buffer A. Cell suspensions were transferred to 1.5 mL screwed cap centrifuge tube and mixed with 300 µL of glass beads. Cells were disrupted by Bead Beater (Biospec, USA) at full speed for 20 seconds. The cell homogenate was transferred to another 1.5 mL centrifuge tube and equal volumes of 2×CTAB buffer (4% CTAB in buffer A) were added. The homogenate was incubated at 65° C. for 2 hr and then extracted with equal volume of phenol:chloroform:isoamyl alcohol (25:24:1). Isopropanol was added to the aqueous phase in a volume equal to ⅔ of the aqueous phase to precipitate genomic DNA. DNA pellet was washed with 75% ethanol and then dried in air.

The primer set (ITS-F CCGTCGCACCTACCGATTGAAT (SEQ ID NO: 4) and ITS-R CCGCTTCACTCGCCGTTACTA (SEQ ID NO: 5) were used to amplify the target sequence from Nannochloropsis strains. PCR was performed at 95° C. for 5 min, 35 cycles of 95° C. 30s, 60° C. 30 s, 72° C. 1 min 30 s, and extension at 72° C. for 10 min. PCR products were cloned into TOPO TA cloning vector (Invitrogen, USA) for sequencing.

Results

Three 1123 bp ITS segments (comprising 18S ribosomal RNA gene, partial sequence; internal transcribed spacer 1, 5.8S ribosomal RNA gene, and internal transcribed spacer 2, complete sequence; and 28S ribosomal RNA gene, partial sequence) were amplified from Nannochloropsis LARB-AZ 0202.0 and the mutants Nannochloropsis LARB-AZ 0202.2, Nannochloropsis LARB-AZ 0202.3 (FIGS. 17, 18 and 19). These sequences showed high similarity with the species belonging to the genus Nannochloropsis as indicated by BLAST search in NCBI (http://blast.ncbi.nlm.nih.gov) (FIG. 20). The maximal identity shared by the ITS sequence of Nannochloropsis LARB-AZ 0202.0 and other known Nannochloropsis spp. is 98%. However, the 2% difference is large enough to distinguish Nannochloropsis LARB-AZ 0202.0 and the mutants derived from it from any other known Nannochloropsis species in the NCBI database, and therefore the ITS sequence obtained from Nannochloropsis LARB-AZ 0202.0 and its mutants can be used as a DNA marker.

Note that seven mutations were detected in Nannochloropsis LARB-AZ 0202.2 (G671, A677, C749, C876, T899, A954, C985) when the sequence was aligned and compared to that of LARB-AZ 0202.0 (C671, G677, G749, A876, C899, G954, T985). Two mutations (i.e., C181, A434) were detected in Nannochloropsis LARB AZ 0202.3 compared to that (i.e., T181, T434) of the wild type. These mutations introduced by mutagenesis can be used as nucleotide markers to distinguish mutants from wild type and to monitor any potential cross contamination between the Nannochloropsis sp. LARB-AZ 0202.0 and its mutants.

REFERENCES

Ackman, R. G., Jangaard, P. M., Hoyle, R. J. and Brockerhoff, H. 1964. Origin of marine fatty acids. I. Analyses of the fatty acids produced by the diatom Skeletonema costatum. J. Fish. Res. Bd. Can. 21: 747-756.
Bigogno et al. Phytochemistry. 2002 July; 60(5):497-503.
Chen et al., 2008.
Chiu et al., Bioresour Technol. 2009 January; 100(2):833-8.
Converti et al., 2009.
Dunstan, G. A., J. K. Volkman, S. M. Barrett, and C. D. Garland. 1993. Changes in the lipid composition and maximization of the polyunsaturated fatty acid content of three microalgae grown in mass culture. J. Appl. Phycol. 5: 71-83.
Emdadi, D. and B. Berland. 1989. Variation in lipid class composition during batch growth of Nannochloropsis salina and Pavlova lutheri. Mar. Chem. 26: 215-225.
Fang Xu, Han-hua Hu, Wei Cong, Zhao-ling Cai, Fan Ouyang, Growth characteristics and eicosapentaenoic acid production by Nannochloropsis sp. in mixotrophic condition, Biotechnology Letters, 2004, 26: 51-53 2004.
Ferreira et al., 2009.
Gouveia L, Oliveira A C Microalgae as raw material for biofuels production. J. 20 Ind. Microbiol. Biotechnol. 36: 269-274 2009.
Hodgson, P. A., Henderson, R. J., Sargent, J. R. & Leftley, J. W. (1991). Patterns of variation in the lipid class and fatty acid composition of Nannochloropsis oculata (Eustigmatophyceae) during batch culture. I. The growth cycle. J. Appl. Phycol., 3: 169-181.
Hsueh et al., Journal of photochemistry and photobiology. B, Biology 2009; 95(1):33-9.
Hu et al., Biotech. Lett 25:421-425, 2003.
Hu et al., Biotech. Lett 28:987-992, 2006.
Kenyon, C. N. 1972. Fatty acid composition of unicellular strains of blue-green algae. J. Bacterid. 109: 827-834
Kobayashi et al., 2008.
Lee, R. F. and Loeblich III, A. R. 1971. Distribution of 21:6 hydrocarbon and its relationship to 22:6 fatty acid in algae. Phytochemistry. 10: 593-602.
Li et al., 2010.
Orcutt, D. M. and Patterson, G. W. 1975. Sterol, fatty acid and elemental composition of diatoms grown in chemically media. Comp. Biochem. Physiol. 50B: 579-583.
Parker, P. L., van Baalen, C. and Maurer, L. 1967. Fatty acids in eleven species of bluegreen algae: geochemical significance. Science. 155: 707-708.
Patil et al., Aquacult Int (2007) Fatty acid composition of 12 microalgae for possible use in aquaculture feed 15:1-9.
Pirt et al. (1983).
Rodolfi et al., Biotechnol Bioeng. 2009 Jan. 1; 102(1):100-12 2009.
Roncarati et al., A. Meluzzi, S. Acciarri, N. Tallarico, and P. Melotti. 2004.
Fatty acid composition of different microalgae strains (Nannochloropsis sp., Nannochloropsis oculata (Droop) Hibberd, Nannochloris atomus Butcher and Isochrysis sp.) according to the culture phase and the carbon dioxide concentration. Journal Of The World Aquaculture Society 35: 401-411 2004.
Samson and Leduy (1985).
Seychelles et al., 2009.
Shan et al., 2009.
Suen, Y., J. S. Hubbard, G. Holzer, and T. G. Tornabene. 1987. Total lipid production of the green alga Nannochloropsis sp. QII under different nitrogen regimes. J. Phycol. 23:289-296.
Tornabene, T. G., Kates, M. and Volcanl, B. E. 1974. Sterol aliphatic hydrocarbons, and fatty acids of a nonphotosynthetic diatom, Nitzschia alba. Lipids. 9: 279-284.
Volkman et al. 1981, Volkman, J. K., Smith, D. J., Eglinton, G., Forsberg, T. E. V. and Corner, E. D. S. 1981. Sterol and fatty acid composition of four marine haptophycean algae. J. Mar. Biol. Ass. U. K. 61: 509-527.
Xu Fang, Zhao-ling Cai, Wei Cong, Fan Ouyang, Growth and fatty acid composition of Nannochloropsis sp. Grown mixotrophically in fed-batch culture, Biotechnology Letters, 26: 2004, 1319-1322.
Xu Fang, Cong Wei, Cai Zhao-Ling, Ouyang Fan, Effects of organic carbon sources on cell growth and eicosapentaenoic acid content of Nannochloropsis sp., Journal of Applied Phycology, 2004.

We claim:

1. A method for producing algal medium chain length fatty acids or hydrocarbons, comprising:
   (a) culturing an algal strain selected from the group consisting of *Nannochloropsis* strain LARB-AZ 0202.0 deposited at ATCC Deposit Number PTA-11048, LARB-AZ 0202.2 deposited at ATCC Deposit Number PTA-11049, LARB-AZ 202.3 deposited at ATCC Deposit Number PTA-11050, and mutants thereof wherein said algal strain produces a first medium chain length fatty acid subset wherein at least 60% of the fatty acids in said subset are of a chain length of C16, wherein the culturing is conducted under conditions suitable to promote production of the first medium chain fatty acid subset; and
   (b) extracting said first medium chain length fatty acid subset from said algal strain to produce a first medium chain length combination, said method optionally further comprising converting said first medium chain length combination extracted from the algal strain into a hydrocarbon fraction and refining the hydrocarbon fraction to produce one or more fractions enriched in C16 medium chain length hydrocarbons.

2. The method of claim 1 further comprising culturing one or more further algal strains that produce a second medium chain length fatty acid subset wherein at least 20% of the fatty acids in said second medium chain length fatty acid subset comprise carbon chain length C10, C12, C14 and C16, wherein the culturing is conducted under conditions suitable to promote production of the second medium chain fatty acid subset.

3. The method of claim 2, wherein the first algal strain and the one or more further algal strains may be cultured as separate cultures or are cultured as a co-culture.

4. The method of claim 1 wherein the method further comprises producing kerosene from the one or more fractions enriched in medium chain length hydrocarbons.

5. A method for producing algal medium chain length fatty acids or hydrocarbons, comprising:
   (a) culturing *Nannochloropsis* strain LARB-AZ 0202.0 deposited under ATCC Deposit Number PTA-11048 and a mutant thereof or a combination of said *Nannochloropsis* strain LARB-AZ 0202.0 and one or more mutants thereof under conditions suitable to promote production of medium chain length fatty acids enriched for C16 fatty acids; culturing a first algal strain selected from the group consisting of *Nannochloropsis* strain LARB-AZ 0202.0 deposited at ATCC Deposit Number PTA-11048, LARB-AZ 0202.2 deposited at ATCC Deposit Number PTA-11049, LARB-AZ 202.3 deposited at or ATCC Deposit Number PTA-11050, and mutants thereof;
   (b) culturing one or more further algal strains that can produce and accumulate large quantities of C14 chain length fatty acids, wherein the culturing is conducted under conditions suitable to promote production of the C14 chain length fatty acids; and
   (c) culturing one or more further algal strains that can produce and accumulate large quantities of C10 and/or C12 chain length fatty acids, wherein the culturing is conducted under conditions suitable to promote production of the C10 and/or C12 chain length fatty acids; and
   (d) extracting oil from said first algal strain and the one or more further algal strains to produce a medium chain length combination; wherein the medium chain length combination comprises carbon chain length C14 and one or more of C10, C12 or C16 fatty acids;
   said method optionally further comprising converting the medium chain length combination into a hydrocarbon fraction and further comprising refining the hydrocarbon fraction to produce one or more fractions enriched in medium chain length hydrocarbons, wherein the one or more fractions comprises one or more fractions enriched in carbon chain length C10, C12, C14 or C16 hydrocarbons.

6. The method of claim 2 further comprising extracting said second medium chain length fatty acid subset from said one or more further algal strains to produce a second medium chain length combination, said method optionally further comprising converting said second medium chain length combination into a second hydrocarbon fraction and refining the second hydrocarbon fraction to produce one or more secondary fractions enriched in C10, C12, C14, or C16 medium chain length hydrocarbons.

7. The method of claim 2 wherein the one or more further algal strains is selected from the group consisting of *Nannochloropsis* sp., *Pinguiococcus pyrenoidosus*, *Aphanocapsa* sp., *Biddulphia aurita*, *Crypthecodinium* sp., *Emiliania huxleyi*, *Nitzschia alba*, *Prymnesiumparvum*, *Skeletonema costatum*, and *Trichodesmium erythraeum*.

8. The method of claim 2 wherein the method further comprises producing kerosene from the one or more fractions enriched in medium chain length hydrocarbons.

9. The method of claim 5 wherein at least one of the one or more further algal strains is selected from the group consisting of *Nannochloropsis* sp., *Pinguiococcus pyrenoidosus*, *Aphanocapsa* sp., *Biddulphia aurita*, *Crypthecodinium* sp., *Emiliania huxleyi*, *Nitzschia alba*, *Prymnesiumparvum*, *Skeletonema costatum*, and *Trichodesmium erythraeum*.

10. The method of claim 5 wherein the first algal strain and the one or more further algal strains may be cultured as separate cultures or are cultured as a co-culture.

11. The method of claim 5 wherein the one or more fractions further comprises one or more fractions enriched in carbon chain length C16 hydrocarbons.

12. The method of claim 5 wherein the method further comprises producing kerosene from the one or more fractions enriched in C10, C12, C14, or C16 medium chain length hydrocarbons.

* * * * *